United States Patent [19]

Nosal et al.

[11] Patent Number: 5,223,539
[45] Date of Patent: Jun. 29, 1993

[54] N,N-DI-ALKYL(PHENOXY)BENZAMIDE DERIVATIVES

[75] Inventors: Roger A. Nosal, Grove; Michael A. Stealey, Libertyville; Richard M. Weiser, Lake Bluff, all of Ill.

[73] Assignee: G. D. Searle & Co., Chicago, Ill.

[21] Appl. No.: 796,513

[22] Filed: Nov. 21, 1991

[51] Int. Cl.$^5$ .................. A61K 31/165; C07C 233/65
[52] U.S. Cl. .................. 514/622; 514/617; 514/618; 514/619; 514/620; 514/621; 514/464; 514/826; 514/886; 549/434; 564/174; 564/176
[58] Field of Search ............... 564/174, 176; 514/617, 514/622, 826, 886, 618, 619, 620, 621

[56] References Cited

U.S. PATENT DOCUMENTS

| | | | |
|---|---|---|---|
| 4,215,114 | 7/1980 | Szmuszkovicz | 424/275 |
| 4,359,476 | 11/1982 | Kaplan et al. | 424/274 |
| 4,360,531 | 11/1982 | McMillan et al. | 424/274 |
| 4,435,332 | 3/1984 | Noguchi et al. | 564/174 |
| 4,466,977 | 8/1984 | McMillan et al. | 424/274 |
| 4,560,549 | 12/1985 | Ritchey | 424/18 |

FOREIGN PATENT DOCUMENTS 63-132869  6/1988  Japan .

OTHER PUBLICATIONS

R. T. Brittain et al. Anti-nociceptive Effects in N-substituted etc. Brit. Pharm. Soc. 49 158P-159P Jul. 1973.
N. J. Harper et al., J. Med. Chem. 17(11) 1188-1193 Jan. 1974.

Primary Examiner—Allen J. Robinson
Assistant Examiner—Shailendra Kumar
Attorney, Agent, or Firm—Mary Jo Kanady; Paul D. Matukaitis

[57] ABSTRACT

The present invention relates to compounds of the formula:

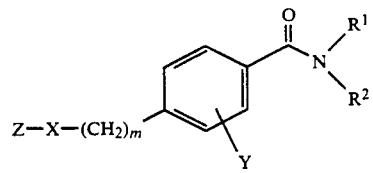

and the pharmaceutically acceptable salts thereof, wherein
Z can be:

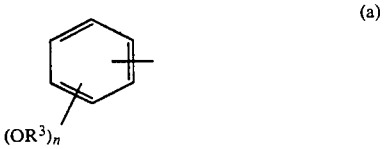

(a)

wherein $R^3$ is alkyl having 1 to 6 carbon atoms and, when n is greater than 1, each $R^3$ can be the same or different; and n is an integer from 1 to 3;
$R^1$ and $R^2$ can each independently be hydrogen, straight or branched chain alkyl, or cycloalkyl having 3 to 8 carbon atoms which can optionally be substituted at one or more positions by alkyl of 1 to 6 carbon atoms; X is oxygen, sulfur, $NR^4$, wherein $R^4$ is hydrogen or alkyl having 1 to 4 carbon atoms, C=O, CHOH, or $CH_2$; Y is hydrogen, alkoxy, halogen, alkyl, or hydroxy; and m is an integer from 0 to 3. The compounds are antagonists of platlet-activating factor (PAF).

28 Claims, No Drawings

N,N-DI-ALKYL(PHENOXY)BENZAMIDE DERIVATIVES

FIELD OF THE INVENTION

This invention is in the field of mammalian therapeutics and relates to compounds for treatment of mammalian diseases such as inflammation, cardiovascular disorders, asthma and other diseases. Of particular interest is a class of N,N-Di-alkyl(phenoxy)benzamide derivatives useful for treatment of cardiovascular and immunoinflammatory related disorders mediated by platelet-activating factor (PAF).

BACKGROUND OF THE INVENTION

Platelet-activating factor (PAF) has been associated with various biological activities and pathways, thus making it an important mediator responsible for a variety of physiological processes including, but not limited to, activation and aggregation of platelets, smooth muscle contraction, pathogenesis of immune complex deposition, inflammation, immunomodulation, respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases, autoimmunization and graft rejection.

SUMMARY OF THE INVENTION

The present invention relates to a novel class of compounds represented by the formula:

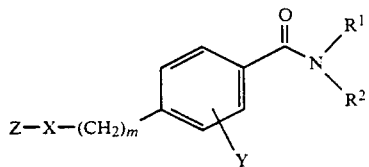

or pharmaceutically acceptable salts thereof, wherein Z can be:

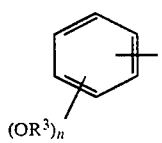

wherein $R^3$ is alkyl having 1 to 6 carbon atoms and, when n is greater than 1, each $R^3$ can be the same or different; and n is an integer from 1 to 3; or

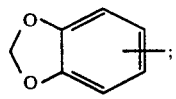

$R^1$ and $R^2$ can each independently be hydrogen, straight or branched chain alkyl of 1 to 10 carbon atoms, or cycloalkyl having 3 to 8 carbon atoms which can optionally be substituted at one or more positions by alkyl of 1 to 6 carbon atoms;

X is oxygen, sulfur, $NR^4$, wherein $R^4$ is hydrogen or alkyl having 1 to 4 carbon atoms, C=O, CHOH or $CH_2$;

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms; and m is an integer from 0 to 3.

The invention further relates to pharmaceutical compositions comprising a compound of formula I and a pharmaceutically acceptable carrier. Such compounds and compositions have potent and specific PAF antagonistic activities and are thereby useful in the treatment of various diseases or disorders mediated by PAF, for example inflammation, cardiovascular disorders, asthma, lung edema, and adult respiratory distress syndrome.

DETAILED DESCRIPTION OF PREFERRED EMBODIMENTS

Preferred embodiments of the present invention are compounds of the formula:

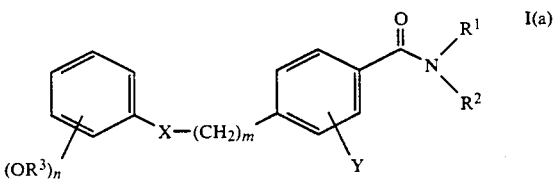

or pharmaceutically acceptable salts thereof, wherein $R^1$ and $R^2$ can each independently be hydrogen, straight or branched chain alkyl of 1 to 10 carbon atoms, or cycloalkyl having 3 to 8 carbon atoms which can optionally be substituted at one or more positions by alkyl of 1 to 6 carbon atoms;

X is oxygen, sulfur, $NR^4$, wherein $R^4$ is hydrogen or alkyl having 1 to 4 carbon atoms, C=O, CHOH, or $CH_2$;

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms;

n is an integer from 1 to 3;

m is an integer from 0 to 3; and $R^3$ is alkyl having 1 to 6 carbon atoms and, when n is greater than 1, each $R^3$ can be the same or different. Included in the present invention are compounds of the formula

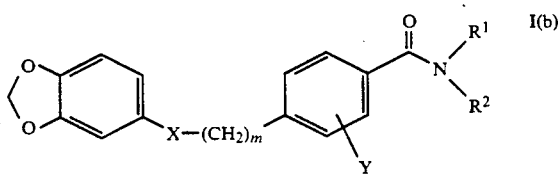

or pharmaceutically acceptable salts thereof, wherein $R^1$ and $R^2$ can each independently be hydrogen, straight or branched chain alkyl of 1 to 10 carbon atoms, or cycloalkyl having 3 to 8 carbon atoms which can optionally be substituted at one or more positions by alkyl of 1 to 6 carbon atoms;

X is oxygen, sulfur, NR⁴, wherein R⁴ is hydrogen or alkyl having 1 to 4 carbon atoms, C=O, CHOH, or CH₂;

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms; and m is an integer from 0 to 3.

Particularly preferred embodiments of the present invention are compounds of the formula:

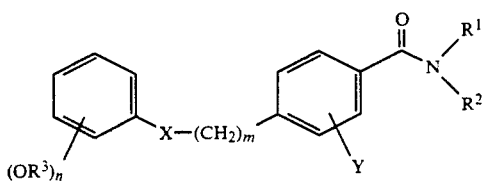

wherein

R¹ and R² are each independently selected from straight or branched chain alkyl having 1 to 6 carbon atoms or cycloalkyl having 3 to 8 carbon atoms which can optionally be substituted at one or more positions by alkyl of 1 to 6 carbon atoms;

Y is hydrogen; alkoxy having 1 to 4 carbon atoms; halogen, wherein the halogen is selected from the group consisting of bromo, fluoro, and chloro; or straight or branched chain alkyl having 1 to 6 carbon atoms;

X is oxygen, C=O, CHOH, or CH₂;

n is an integer from 1 to 3;

m is an integer from 0 to 3; and

R₃ is alkyl having 1 to 4 carbon atoms and, when n is greater than 1, each R³ can be the same or different.

Further embodiments of the present invention are compounds of the formula:

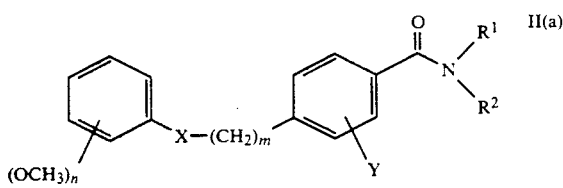

wherein

R¹ and R² are each independently selected from straight or branched chain alkyl having 1 to 6 carbon atoms or cycloalkyl having 4 to 6 carbon atoms;

Y is hydrogen; alkyoxy having 1 to 4 carbon atoms; or alkyl having 1 to 4 carbon atoms;

X is oxygen, C=O, CHOH, or CH₂;

n is an integer from 1 to 3; and m is 0 or 1.

Also included in the present invention are p-bromobenzamide compounds of the formula

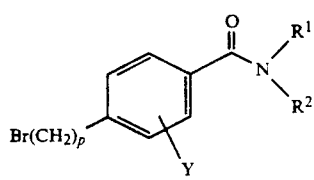

wherein

R¹ and R² can each independently be hydrogen, straight or branched chain alkyl having 1 to 10 carbon atoms or cycloalkyl having 3 to 8 carbon atoms which can optionally be substituted at one or more positions by alkyl of 1 to 6 carbon atoms;

p is an integer from 0 to 3; and

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms.

Intermediates of Formula III are useful in making the compounds of the present invention.

Preferred intermediates are those compounds of the formula

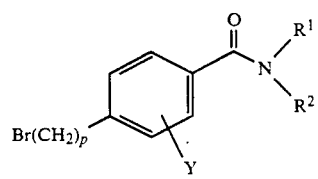

wherein

R¹ and R² can each independently be hydrogen, straight or branched chain alkyl having 1 to 6 carbon atoms or cycloalkyl having 4 to 6 carbon atoms which can optionally be substituted at one or more positions by alkyl of 1 to 4 carbon atoms; and p is 0 or 1; and Y is hydrogen, alkoxy having 1 to 4 carbon atoms, or alkyl having 1 to 4 carbon atoms.

As used herein the term "alkyl having 1 to 10 carbon atoms": refers to straight chain or branched chain hydrocarbon groups having from one to ten carbon atoms. Illustrative of such alkyl groups are methyl, ethyl, propyl, isopropyl, butyl, t-butyl, isobutyl, pentyl, neopentyl, hexyl, isohexyl, octyl, decyl and the like.

As used herein the term "cycloalkyl having 3 to 8 carbon atoms" includes cycloalkyl groups having from three to eight carbons. Illustrative of such cycloalkyl groups are cyclopropyl, cyclobutyl, cyclopentyl, cyclohexyl, cycloheptyl, cyclooctyl and the like.

As used herein the term halogen includes fluoro, chloro and bromo.

As used herein the term "alkoxy wherein the alkyl is 1 to 6 carbon atoms" refers to straight or branched chain ethers. Illustrative of such groups are methoxy, ethoxy, propoxy, butoxy, isopropoxy, pentoxy, hexyloxy, and the like.

Included within the embodiments of the present invention are the tautomeric forms of the described compounds, isomeric forms including geometric isomers, enantiomers and diastereoisomers, and the pharmaceutically acceptable salts thereof.

The term "pharmaceutically acceptable salt" refers to a salt prepared by contacting a compound of formula (I) with an acid or base whose anion or cation is generally considered suitable for human consumption. Examples of pharmacologically acceptable salts include but are not limited to the hydrochloride, hydrobromide, hydroiodide, sulfate, phosphate, acetate, propionate, lactate, maleate, malate, succinate, tartrate, sodium, potassium and lithium salts. Other pharmaceutically acceptable salts are listed in *Reminotons's Pharmaceutical Sciences*, 17th Edition (1985) p. 1418-1419, incorporated herein by reference. All of these salts may be prepared by conventional means by reacting, for example, the appropriate acid or base with the corresponding compound of Formula I.

The compounds of formula (I) and the intermediates used to make them may be prepared in accordance with the procedures shown in Schemes A, B, C, D, and E.

SCHEME A

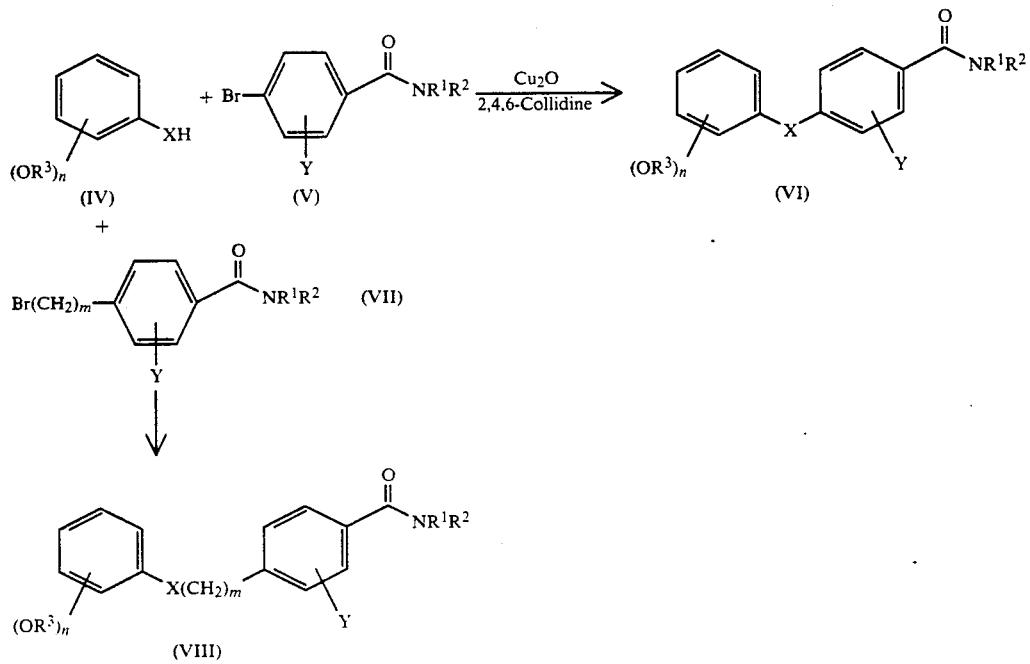

X = O, S, NH
Y = H, alkoxy, halogen, or alkyl
m = 0 to 3
n = 1 to 3
$R^1, R^2$ = alkyl, cycloalkyl, or substituted cycloalkyl
$R^3$ = alkyl

SCHEME B

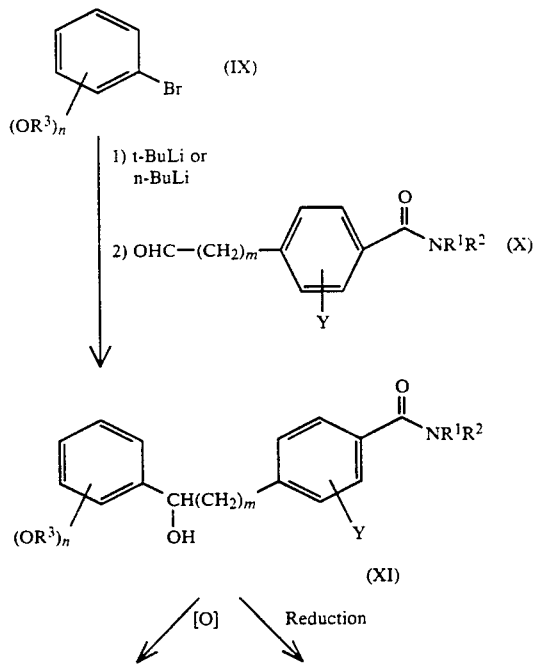

SCHEME B

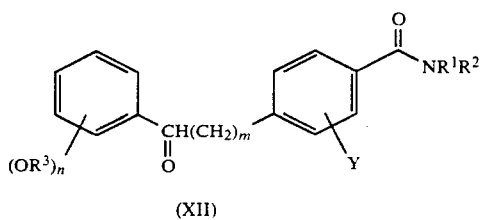
(XII)

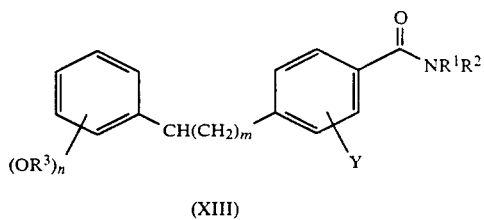
(XIII)

Y = H, alkoxy, halogen, or alkyl
m = 0 to 3
n = 1 to 3
$R^1, R^2$ = alkyl, cycloalkyl, or substituted cycloalkyl
$R^3$ = alkyl

SCHEME C

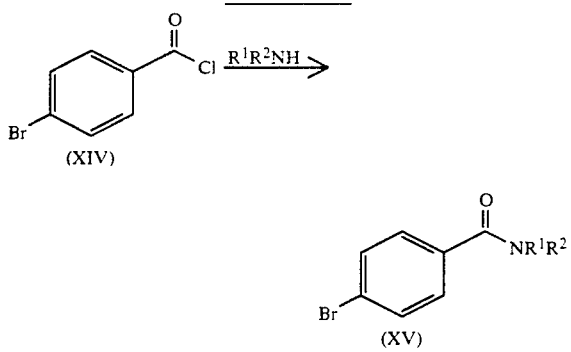

$R^1R^2$ = alkyl, cycloalkyl, or substituted cycloalkyl

SCHEME D

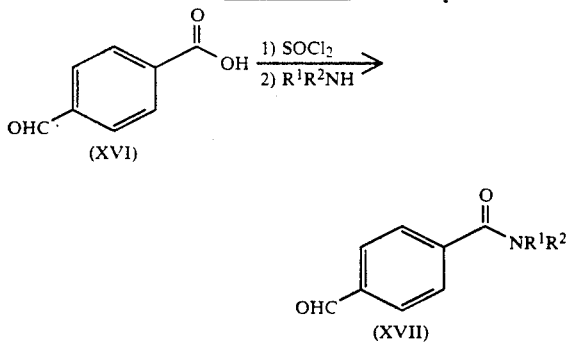

SCHEME E

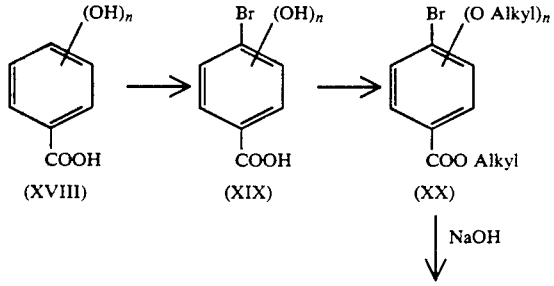

-continued SCHEME E

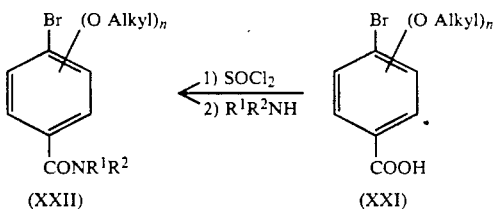

Scheme A describes the reaction of a substituted phenol, thiophenol or aniline (IV) with a bromobenzamide (V) in 2,4,6-collidine using cuprous oxide as a catalyst to give a phenoxy, phenylthio, or phenylaminobenzamide of formula (VI). Substitution of the bromoalkylbenzamide (VII) for (V) gives the phenoxyalkyl, phenylthioalkyl or phenylaminoalkyl benzamides of formula (VIII).

Preferred reaction conditions for the procedure of Scheme A include refluxing the suspension of $Cu_2O$ in a solution of the aryl bromide V and phenol IV in 2,4,6-collidine for 18-30 hr. In the case where the bromide is structure VII, these conditions may also be used, but preferred conditions are to simply stir a suspension of $K_2CO_3$ in a solution of phenol IV and bromide VII in dimethylformamide at room temperature for 16-30 hrs.

In the $Cu_2O$ procedure, the reaction is worked up by diluting with HCl and extracting with ethyl acetate. The resultant organic layer is washed successively with aqueous NaCl solution, aqueous NaOH solution and aqueous NaCl solution. The dried organic layer is stripped in vacuo and the residue chromatographed on silica gel using mixtures of ethyl acetate and hexane as eluents to give the product VI. When the bromide is VII, the reaction is worked up by diluting with water and extracting with ethyl acetate. The crude product isolated from the dried organic layer is purified by chromatography on silica gel to give pure VIII.

Scheme B shows the preparation of compounds of Formula I in which (X) is C=O, CHOH, or $CH_2$. An alkoxy-bromophenyl derivative (IX) is reacted with t-or n- butyl lithium to give an aryl lithium species which is then reacted with a formyl or formyl alkyl benzamide of formula (X) to give the phenyl(hydroxy)alkyl benzamide of formula (XI). The compound (XI) may then be oxidized to give a benzoyl or benzamide of formula (XII) or it may be reduced to give the phenylalkyl benzamide of formula (XIII).

In Scheme B, preferred reaction conditions for the formation of the aryl lithium species are to treat a solution of the aryl bromide (IX) in an ethereal solvent such as diethyl ether or tetrahydrofuran or mixtures thereof with an alkyl lithium reagent such as n-butyl or tert-butyl lithium in the cold at −70° to 0°. A solution of aldehyde X in an etheral solvent such as diethyl ether or tetrahydrofuran or mixtures thereof is then added to produce XI. The reaction is quenched with a protic reagent such as aqueous HCl. The product XI, after purification by chromatography on silica gel, is reduced by an appropriate chemical means to give compound XIII. One method of reduction is, for example, hydrogenation in the presence of an acid such as sulfuric acid in an organic solvent such as ethanol. A suitable catalyst is 5% Pd/C. Purification of the crude product on silica gel gives the desoxy compound XIII. Ketone XII is synthesized by reaction of alcohol XI with a suitable oxidizing agent such as pyridinium chlorochromate. Crude XII is purified by chromatography on silica gel.

Scheme C shows the reaction of a bromobenzoyl chloride (XIV) with an amine ($R^1R^2NH$) to give the bromo benzamide intermediate of formula (XV).

Preferred reaction conditions for procedure of Scheme C include treatment of a cold (−20° to 0°) solution of acid chloride XIV in an inert solvent such as tetrahydrofuran with a solution of a 2 molar excess of the desired amine $R^1R^2NH$. The reaction is warmed to temperatures ranging from room temperature to 67° for from 1 to 6 hrs. The reaction is worked up by concentration in vacuo, adding water to the residue and extracting with a suitable organic solvent such as diethyl ether. The organic solution of crude product is washed with an aqueous acid solution such as 0.5N HCl and an aqueous base solution such as 5% $NaHCO_3$. The crude product obtained from the organic solution is further purified by chromatography on silica gel to give pure amide XV.

In another preferred procedure, amides XV may also be synthesized by treatment of a cold (−10° to 10°) solution of 1 molar equivalent each of triethylamine and $R^1R^2NH$ in an inert solvent such as tetrahydrofuran with a solution of acid chloride XIV in an inert solvent such as tetrahydrofuran. After stirring at room temperature for 12 to 24 hrs., the reaction is diluted with water and extracted with a suitable solvent such as ethyl acetate. The organic layer is washed successively with an acid such as 0.5N $KHSO_4$ and an aqueous basic solution such as 5% $NaHCO_3$. The crude product isolated from the organic layer may be sufficiently pure for further use. Alternatively, purification is effected by chromatography on silica gel.

Scheme D shows the reaction of the formyl benzoic acid (XVI) with thionyl chloride and an amine ($R^1R^2NH$) to give the formyl benzamide of formula (XVII).

Preferred reaction conditions for the procedure of Scheme D include reaction of acid XVI with a chlorinating agent such as thionyl chloride in an inert solvent such as benzene containing a small amount of dimethylformamide. The reaction mixture is refluxed for 2 to 8 hrs. The intermediate acid chloride is isolated by removal of solvents in vacuo and azeotroping with benzene to remove last traces of the chlorinating agent. The acid chloride is converted to amides XVII in the same manner as for the synthesis of amides XV from XIV. The reaction is worked up by diluting with water and an aqueous base such as 0.07N NaOH and extracting the aqueous layer with an organic solvent such as ethyl acetate. The crude amide XVII thus isolated is suitable for use without further purification.

Scheme E shows the reaction of (XXI) with $SOCl_2$ followed by an amine ($R^1R^2NH$) gives a bromoalkoxy benzamide of formula (XXII).

Preferred reaction conditions for the procedure of Scheme E are to reflux a solution of 4-bromo-3-alkoxybenzoic acid XXI in a chlorinating agent such as thionyl chloride for 1 to 3 hrs. The chlorinating agent is removed in vacuo and the residue is azeotroped with a solvent such as toluene to remove last traces of the chlorinating agent. The acid chloride was converted to amides XXII by combining a solution of it in a solvent such as tetrahydrofuran to a cold (−10° to 10°) solution of one molar equivalent each of triethylamine and $R^1R^2NH$ in tetrahydrofuran. The reaction is stirred at room temperature for 12 to 24 hrs. and the resultant precipitate is filtered and the filtrate concentrated in vacuo. The residue is dissolved in a suitable solvent such as ethyl acetate and washed successively with an acid such as 1N HCl and a base such as aqueous $NaHCO_3$. The crude product isolated from the organic layer is purified by chromatography on silica gel to give pure XXII.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of a compound of Formula (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, a compound of Formula (I) may be administered orally, topically, parenterally, or by inhalation spray or rectally in dosage unit formulations containing conventional non-toxic pharmaceutically acceptable carriers, adjuvants and vehicles. The term parenteral as used herein includes but is not limited to subcutaneous, intravenous, intramuscular, intrasternal, infusion techniques or intraperitoneally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is selected in accordance with a variety of factors, including the type, age, weight, sex and medical condition of the patient; the severity of the infection; the route of administration; and the particular compound employed and thus may vary widely.

Dosage levels of the order from about 0.01 mg to about 100 mg per kilogram of body weight per day are useful in the treatment of the above-indicated conditions (from about 0.5 mg to about 5 gs. per patient per day). Dosages of from about 0.01 mg to about 50 mg per kilogram of body weight per daily dosage are preferred (about 0.5 mg to about 2.5 gm per patient per day).

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules which may be taken singly or multiply. These may with advantage contain an amount of active ingredient from about 0.5 to 250 mg preferably from about 0.5 to 150 mg. A suitable daily dose for a mammal may vary widely depending on the condition of the patient and other factors. However, a dose of from about 0.01 to 100 mg/kg body weight, particularly from about 0.01 to 75 mg/kg body weight may be appropriate.

The active ingredient may also be administered by injection as a composition wherein, for example, saline, dextrose or water may be used as a suitable carrier. A suitable daily dose is from about 0.01 to 100 mg/kg body weight injected per day in single or multiple doses or continuous infusion depending on the disease being treated. A preferred daily dose would be from about 0.01 to 50 mg/kg body weight.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The amount of active ingredient that may be combined with the carrier materials to produce a single dosage form which may be taken singly or multiply will vary depending upon the host treated and the particular mode of administration. For example, a formulation intended for the oral administration of humans may contain from 0.5 mg to 250 mg of active agent compounded with an appropriate and convenient amount of carrier material which may vary from about 5 to 95 percent of the total composition. Dosage unit forms will generally contain between from about 0.5 mg to about 150 mg of active ingredient.

The following examples are intended to further illustrate the present invention and not to limit the invention in spirit or scope. In the examples, all parts are parts by weight unless otherwise expressly set forth.

The biological activity of the compounds of the present invention was determined using the following tests.

PAF-INDUCED PLATELET AGGREGATION AND SECRETION

Washed, [$^3$H]serotonin-labeled rabbit platelets were prepared as previously described in COX, C. P., J. LINDEN and S. I. SAID: VIP elevates platelet cyclic AMP (cAMP) levels and inhibits in vitro platelet activation induced by platelet- activating factor (PAF). *Peptides* 5:25-28, 1984, and maintained in an atmosphere of 5% $CO_2$ at 37° C. until used in the bioassay. Aliquots of platelets ($2.5 \times 10^8$/ml) were incubated with either an antagonist of PAF or the appropriate vehicle for 60 sec prior to the addition of PAF (0.2 nM to 0.2 mM). Aggregation was continuously monitored on a strip-chart recorder and recorded as the height of the tracing at 60 sec after the the addition of PAF. Secretion of [$^3$H]serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated 12-15 times, using several different platelet preparations. $IC_{50}$ values were determined by inspection of the dose-response curves.

INHIBITION OF $^3$H-PAF BINDING TO HUMAN PLATELET MEMBRANE RECEPTORS

Receptor Preparation

Ten units of in-dated human packed platelets, each containing 45-65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM ($2300 \times g$). Plasma was decanted and the platelets were resuspended in 35 ml of buffer (10 mM Trizma 7.0, 2 mM EDTA (dipotassium salt), and 150 mM KCl) and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM $CaCl_2$. Following centrifugation, the buffer was decanted and the pellets were resuspended in the $CaCl_2$ buffer, avoiding erythrocyte contamination by recovering less than 100% of the platelet pellets. The resuspended platelets were dispensed in 8-10 ml aliquots into Corex tubes and disrupted by three cycles of freezing (dry ice/ethanol) and thawing (24° C.). The tubes were centrifuged at 40,000 × g for 20 minutes at 4° C. Supernatants were decanted and each pellet was resuspended in 5-7 ml 10 mM Trizma 7.0. All resuspended pellets were pooled and aliquots of about 1200 ml were dispensed into 1.5 ml microfuge tubes and frozen at −70° C. Protein content was determined by a fluorescamine protein assay.

Assay Methods: Receptor Characterization—Each receptor preparation was evaluated to determine the number of receptor populations, the number of PAF receptor equivalents/mg protein and the dissociation constant ($K_D$) for PAF binding This required 2-3 experiments in which the protein concentration was held constant and the $^3$H-PAF ligand concentration was varied from approximately 0.10-2.5 nM and the data was analyzed by Scatchard methodology. Total incubation volume was 250 ml for these procedures and incubations were conducted at 24° C. for 30 minutes. For further experimentation, total incubation volumes are 500 ml. Protein and ligand concentrations were adjusted to give 0.075 nM receptor equivalents in the presence of 0.75 nM $^3$H-PAF. Each receptor preparation was then used to determine the dose - response displacement relationship of unlabeled PAF and the PAF antagonist, triazolam. As long as the $K_D$ value and $IC_{50}$ values for PAF and triazolam were consistent With similar data collected from past receptor preparations used in the assay, the new receptor preparation was used for evaluating compounds.

Assay Methods: Routine Assay of Compounds—The compounds were weighed precisely and solubilized in quantities of DMSO such that a 5 ml aliquot in the incubate would deliver the desired compound concentration. Compounds tested for the first time in this assay were evaluated at a concentration of 50 mM in the incubation medium. All compounds were generally solubilized in DMSO for about 2 hours prior to assay. Triazolam was always included in each screening assay as a compound inhibition control. A standard concentration of 50 mM inhibited $^3$H-PAF binding by approximately 50%. Nonspecific binding control solution was made by drying to completion about 26.2 ml unlabeled PAF under a stream of argon. PAF was resolubilized in 1000 ml DMSO. When delivered in a 5 ml aliquot, the final concentration of 1 mM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM $CaCl_2$). Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 ml of stock $^3$H-PAF (DuPont NEN, NET-668) to 14 ml of assay buffer. Since the amount of $^3$H-PAF in the final incubate was to be 0.75 nM, the actual amount of stock $^3$H-PAF to be used had to be determined for each lot of material based upon its specific activity.

Membrane receptors for assay were prepared by thawing the appropriate number of tubes at room temperature and adding membranes to 10 mM Trizma 7.0 containing 10 mM $CaCl_2$. A total volume of 14 ml Was made. The actual amount of membranes needed was determined by the requirement to have 0.075 nM PAF receptor equivalents per assay tube. All materials were kept in motion by rocking on a rocker plate.

First, 5 ml of compound or DMSO was added to each 12×75 mm polypropylene tube, followed by the addition of 95 ml assay buffer. Next, 200 ml $^3$H-PAF was added to each tube and 3 aliquots of $^3$H-PAF taken at different times during the dispensing were placed in scintillation vials. The reaction was initiated by the addition of 200 ml of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 ml total volume of incubate. This consisted of 5 ml drug with DMSO or only DMSO, 95 ml assay buffer, 200 ml $^3$H-PAF (0.75 nM final concentration) and 200 microleters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 mM, or to run dose-response determinations for a compound. In general, dose-response curves were composed of 4 compound doses designed to inhibit $^3$-PAF binding by 15-85%, with at least 1 dose on each side of the 50% point.

Routine Assay Calculations

Triplicate DPM determinations (corrected for background) within a single compound dose were averaged while all 6 determinations of total binding ("0" dose, DMSO only) were averaged. The amount for nonspecific binding (1 mM PAF) was subtracted from all the dose averages, giving an amount of specific binding in all cases. The percent displacement of $^3$H-PAF or inhibition of binding was calculated by the formula STBo-SBc/STBo ×100, where STBo=specific binding of "0" dose controls and SBc=specific binding in the presence of compound. If a compound tested at the initial screening dose of 50 mM inhibited binding by 45% or more, the compound was considered active and was tested in a dose-response manner to determine an $IC_{50}$ value.

Compounds inhibiting PAF binding by less than 45% at a 50 mM concentration were considered inactive and no further testing was done.

$IC_{50}$ values were determined on active compounds in subsequent tests. Three or more compound doses must inhibit $^3$H-PAF binding between 15-85%. Using a computer program, % displacement data was transformed (logit) and a least squares linear regression was performed on the data meeting the 15-85% requirement to determine $IC_{50}$ values from data points derived from the same assay.

| Compound Example No. | PAF induced platelet secretion ($IC_{50}$) (M) | PAF induced platelet aggregation ($IC_{50}$) (M) | Inhibition of $^3$H-PAF Binding to Human Platelet ($IC_{50}$) (μM) |
|---|---|---|---|
| 1 | $8.9 \times 10^{-9}$ | $10^{-7}$ to $10^{-8}$ | 0.133 |
| 2 | $1116.3 \times 10^{-9}$ | $10^{-5}$ to $10^{-6}$ | 22.1 |
| 3 | $750 \times 10^{-9}$ | $10^{-5}$ to $10^{-6}$ | 10.5 |
| 4 | $9.36 \times 10^{-9}$ | $10^{-5}$ to $10^{-6}$ | 0.508 |

| Compound Example No. | PAF induced platelet secretion (IC$_{50}$) (M) | PAF induced platelet aggregation (IC$_{50}$) (M) | Inhibition of $^3$H-PAF Binding to Human Platelet (IC$_{50}$) (μM) |
|---|---|---|---|
| 5 | 4.01 × 10$^{-6}$ | 10$^{-5}$ to 10$^{-6}$ | 1.499 |
| 6 | 85.9 × 10$^{-9}$ | 10$^{-6}$ to 10$^{-7}$ | 2.01 |
| 7 | 422 × 10$^{-9}$ | 10$^{-5}$ to 10$^{-6}$ | 0.914 |
| 8 | 2573 × 10$^{-9}$ | 10$^{-4}$ to 10$^{-5}$ | 44%* |
| 9 | 1489 × 10$^{-9}$ | 10$^{-5}$ to 10$^{-6}$ | 61.9%* |
| 10 | 10$^{-5}$ to 10$^{-6}$ | >10$^{-5}$ | 47%* |
| 11 | 114 × 10$^{-9}$ | 10$^{-5}$ to 10$^{-6}$ | 1.48 |
| 12 | 142 × 10$^{-9}$ | 10$^{-5}$ to 10$^{-6}$ | 2.71 |
| 13 | 89.4 × 10$^{-9}$ | <10$^{-6}$ | 0.6 |
| 14 | 1807 × 10$^{-9}$ | 10$^{-6}$ to 10$^{-7}$ | 49.2%* |
| 15 | 26.6 × 10$^{-9}$ | 10$^{-6}$ to 10$^{-7}$ | 0.425 |
| 16 | 103 × 10$^{-9}$ | 10$^{-6}$ to 10$^{-7}$ | — |
| 17 | 631.9 × 10$^{-9}$ | 10$^{-5}$ to 10$^{-6}$ | 3.71 |
| 18 | 1990 × 10$^{-9}$ | 10$^{-5}$ to 10$^{-6}$ | 8.16 |
| 19 | — | — | 0.995 |
| 20 | — | — | 41%* |
| 21 | — | — | 11.2 |
| 22 | >10$^{-5}$ | 10$^{-4}$ to 10$^{-5}$ | 53.2 |
| 23 | 10$^{-4}$ to 10$^{-5}$ | 10$^{-4}$ to 10$^{-5}$ | >50 |

*Percent Inhibition at 50 μM

EXAMPLE 1

N-cyclohexyl-N-(1-methylethyl)-4-(3,4,5-trimethoxyphenoxy)benzamide

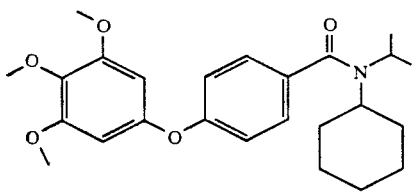

A slurry of cuprous oxide (300 mg, 2.1 mmol) in a solution of 3,4,5-trimethoxyphenol (736 mg, 4.0 mmol) and 4-bromo-N-isopropyl-N-cyclohexyl benzamide (1.290 g, 3.98 mmol) in 2,4,6-collidine (20 ml) was refluxed with stirring under a nitrogen atmosphere for 18 hr. The reaction was cooled, poured onto dilute aqueous HCl and extracted three times with ethyl acetate. The combined organic layers were washed twice with saturated aqueous NaCl solution, twice with 5% NaOH solution, twice with saturated NaCl solution and dried (Na$_2$SO$_4$). The drying agent was filtered and the filtrate concentrated in vacuo to give 1.29 g of crude product. This material was chromatographed on silica gel using mixtures of ethyl acetate and hexane as the eluents to give the title compound as a crystalline solid that could be recrystallized from ethyl acetate hexane, melting point 124.01° C. (DSC).

Anal. Calcd. for C$_{25}$H$_{33}$NO$_5$: C, 70.23; H, 7.78; N, 3.28. Found: 70.24; H, 8.06; N, 3.25.

EXAMPLE 2

N-cyclohexyl-4-(4-methoxyphenoxy)-N-(1-methylethyl)benzamide

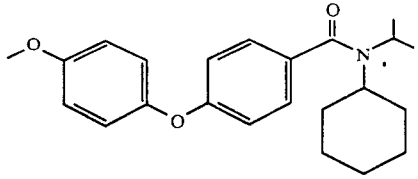

The reaction and workup were carried out in the same manner as described in Example 1 using p-bromobenzoic acid N-isopropyl-N-cyclohexyl amide (1.751 g, 5.40 mmol), 4-methoxy phenol (715 mg, 5.76 mmol) and cuprous oxide (390 mg, 2.73 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 81.73° C. (DSC)

Anal. Calcd. for C$_{23}$H$_{29}$NO$_3$: C, 75.17; M, 7.95; N, 3.81. Found: C, 74.82; H, 7.98; N, 3.76.

EXAMPLE 3

N-cyclohexyl-4-(3-methoxyphenoxy)-N-(1-methylethyl)benzamide

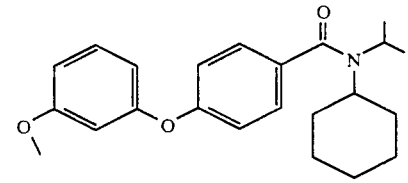

The reaction and workup were carried out in the same manner as described in Example 1 using p-bromobenzoic acid N-isopropyl-N-cyclohexyl amide (1.798 g, 5.54 mmol), 3-methoxy phenol (769 mg, 6.19 mmol) and cuprous oxide (403 mg, 2.82 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 101.24° C. (DSC).

Anal. Calcd. for C$_{23}$H$_{29}$NO$_3$: C, 75.17; H, 7.95; N, 3.81. Found: C, 74.83; H, 8.12; N, 3.52.

EXAMPLE 4

N-cyclohexyl-N-cyclopentyl-4-(3,4,5-trimethoxyphenoxy)benzamide

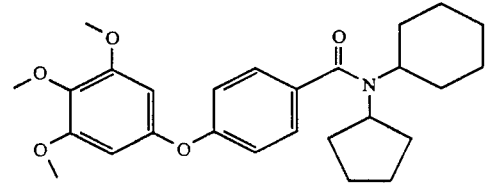

The reaction and workup were carried out in the same manner as described in Example 1 using p-bromobenzoic acid N-cyclopentyl-N-cyclohexyl amide (2.285 g, 6.52 mmol), 3,4,5-trimethoxy phenol (1.199 g, 6.51 mmol) and cuprous oxide (486 mg, 3.40 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 166.16° C. (DSC).

Anal. Calcd. for $C_{27}H_{35}NO_5$: C, 71.50; H, 7.78; N, 3.09. Found: C, 71.57; H, 7.77; N, 3.09.

EXAMPLE 5

N-cyclohexyl-N-cyclopentyl-4-(3,4-dimethoxyphenoxy)benzamide

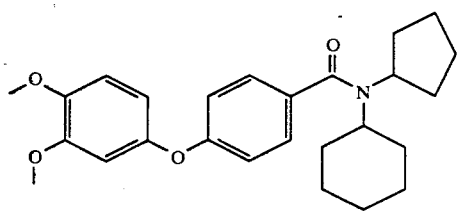

The reaction and workup were carried out in the same manner as described in Example 1 using p-bromobenzoic acid N-cyclopentyl-N-cyclohexyl amide (2.350 g, 6.71 mmol), 3,4-dimethoxy phenol (1.051 g, 6.81mmol) and cuprous oxide (478 mg, 3.34 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 153.96° C. (DSC).

Anal. Calcd. for $C_{26}H_{33}NO_4$: C, 73.73; H, 7.85; N, 3.31. Found: C, 73.30; H, 7.97; N, 3.25.

EXAMPLE 6

N-cyclohexyl-4-(3,4-dimethoxyphenoxy)-N-(1-methylethyl)benzamide

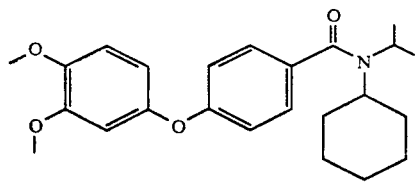

The reaction and workup were carried out in the same manner as described in Example 1 using p-bromobenzoic acid N-isopropyl-N-cyclohexyl amide (2.820 g, 8.70 mmol), 3,4-dimethoxy phenol (1.347 g, 8.74 mmol) and cuprous oxide (647 mg, 4.52 mmol) in 2,4,6-collidine (20 ml). The crude product was chromatographed on silica gel using mixtures of ethyl acetate and hexane as eluents to give the title compound as a crystalline solid that could be recrystallized from ethyl acetate and hexane, m. pt. 106.85° C. (DSC).

Anal. Calcd. for $C_{24}H_{31}NO_4$: C, 72.52; H, 7.86; N, 3.52. Found: C, 72.20; H, 7.96; N, 3.48.

EXAMPLE 7

N,N-dicyclopentyl-4-(3,4-dimethoxyphenoxy)benzamide

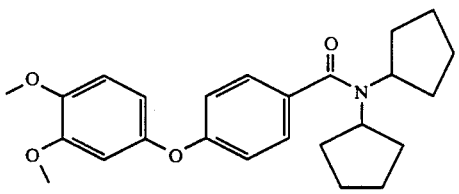

The reaction and workup were carried out in the same manner as described in Example 1 using p-bromobenzoic acid N,N-dicyclopentyl amide (1.839 g, 5.47 mmol), 3,4-dimethoxy phenol (876 mg, 5.68 mmol) and cuprous oxide (413 mg, 2.89 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 179.95° C. (DSC).

Anal. Calcd. for $C_{25}H_{31}NO_4$: C, 73.32; H, 7.63; N, 3.42. Found: C, 73.20; H, 7.54; N, 3.39.

EXAMPLE 8

N-cyclohexyl-4-[(3,4-dimethoxyphenyl)hydroxymethyl]-N-(1-methylethyl)benzamide

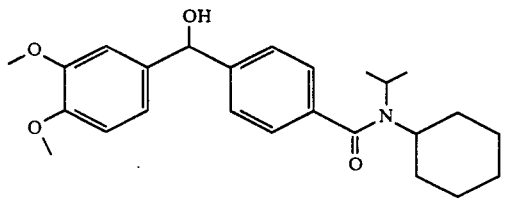

To a stirred solution of 4-bromoveratrole (0.77 ml, 6.0 mmol) in ethyl ether (30 mL) at 0° C. under an argon atmosphere was added n-butyl lithium (3.75 mL of 1.6 M solution in hexane). A white precipitate formed and tetrahydrofuran (THF) (10 mL) was added. The reaction mixture was cooled to −20° C. and a solution of terephthalaldehydic acid N-isopropyl-N-cyclohexyl amide (0.82 g, 3.0 mmol) in THF: ethyl ether (4:3, 35 mL) was added rapidly. Thin layer chromatography (TLC) (50% ethyl acetate/hexane) after 5 min showed the reaction was nearly complete. The reaction was quenched at −15° C. by adding water (50 mL) and 1N HCl(20 mL). The reaction was further diluted with water (300 mL) and extracted three times with ethyl acetate (50 mL portions). The combined extracts were washed twice with saturated NaCl solution and dried (MgSCO4). The drying agent was filtered and the filtrate concentrated in vacuo to give the crude product. The crude product was chromatographed on silica gel using mixtures of ethyl acetate and hexane as eluents to give the title compound as an amorphous solid.

NMR (ppm, CDCl3): 0.98-1.85 (16H, multiplet, hydrocarbon envelope); 3.82 (3H, s, OMe); 3.86, (3H, s, OMe); 5.81 (d, 1H, J=5 Hz, benzylic); 2.30 (1H, d, J=5 Hz, OH); 7.39 (2H, d, J=9 Hz, phenyl); 7.28 (2H, d, J=9 Hz); 6.89 (1H, d, J=7 Hz, phenyl); 6.83 (1H, d, J=7Hz, phenyl)

Anal. Calcd. for $C_{25}H_{33}NO_4$: C, 72.96; H, 8.08; N, 3.40. Found: C, 72.13; H, 8.21; N, 3.40.

EXAMPLE 9

N-cyclohexyl-N-cyclopentyl-4-[(3,4-dimethoxyphenyl)hydroxymethyl]benzamide

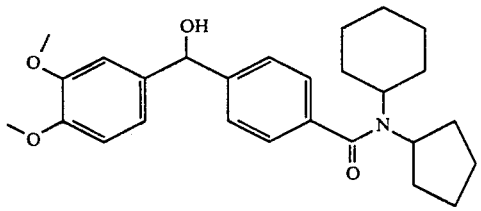

The reaction and workup were carried out in the same manner as described in Example 8, using 4-bromoveratrole (0.9 mL, 7.0 mmol), n-butyl lithium (4.38 mL of 1.6 M solution in hexane), terephthalaldehydic acid N-cyclopentyl-N-cyclohexyl amide (1.9 g, 6.36 mmol). The crude product was chromatographed on silica gel using mixtures of ethyl acetate and hexane to give the title compound as an amorphous solid.

Anal. Calcd. for $C_{27}H_{35}NO_4$: C, 74.11; H, 8.06; N, 3.20. Found: C, 73.72; H, 8.20; N, 3.09.

EXAMPLE 10

N,N-dicyclopentyl-4-[(3,4-dimethoxyphenyl)hydroxymethyl]benzamide

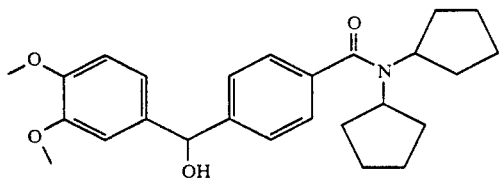

The reaction and workup were carried out in the same manner as described in Example 8 using 4-bromoveratrole (1.29 mL, 10 mmol), n-butyl lithium (6.25 mL of 1.6 M solution in hexane), terephthalaldehydic acid N,N-dicyclopentyl amide (Example 29) (2.6 g, 9.1 mmol). The crude product was chromatographed on silica gel using mixtures of ethyl acetate and hexane to give the title compound as an oil that crystallized under ethyl ether: m. pt. 137–138° C.

Anal. Calcd. for $C_{26}H_{33}NO_4$: C, 73.73; H, 7.85; N, 3.31. Found: C, 73.20; H, 7.93; N, 3.29.

EXAMPLE 11

N,N-dicyclopentyl-4-[(3,4-dimethoxyphenyl)methyl]benzamide

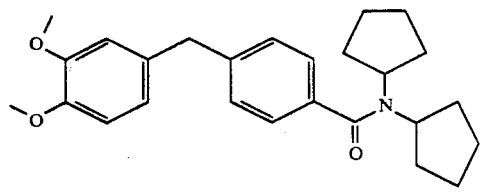

The compound prepared in Example 10 (0.40 g, 0.84 mmol) in ethyl alcohol (20 mL) containing concentrated sulfuric acid (2 drops) was hydrogenated at 60 psi and room temperature using 5% Pd/C as catalyst. The catalyst was filtered and the filtrate concentrated in vacuo to give the crude product as an oil. Chromatography of the crude product on silica gel using mixtures of ethyl acetate and hexane as eluents gave the title compound as a crystalline solid, m. pt. 138–142° C.

NMR (CDCl$_3$, ppm): 1.38-2.27 (16H, hydrocarbon envelope); 3.82 (3H, s, OMe); 3.86 (3H, s, OMe); 3.93 (2H, s, benzylic); 7.28 (2H, d, J=8 Hz, phenyl); 7.18 (2H, d, J=8 Hz, phenyl).

Anal. Calcd. for $C_{26}H_{33}NO_3$: C, 76.62; H, 8.16; N, 3.44. Found: C, 75.94; H, 8.22; N, 3.32.

EXAMPLE 12

N-cyclohexyl-4-(3,5-dimethoxyphenoxy)-N-(1-methylethyl)benzamide

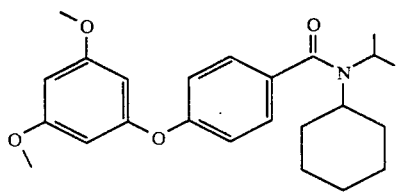

The reaction and workup were carried out in the same manner as described in Example 1 using p-bromobenzoic acid N-isopropyl-N-cyclohexyl amide (2.353 g, 7.26 mmol), 3,5-dimethoxy phenol (1.061 g, 6.88 mmol) and cuprous oxide (492 mg, 3.44 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 140.12° C. (DSC).

Anal. Calcd. for $C_{24}H_{31}NO_4$: C, 72.52; H, 7.86; N, 3.52. Found: C, 72.61; H, 8.04; N, 3.46.

EXAMPLE 13

N-cyclohexyl-N-cyclopentyl-3-methyl-4-(3,4,5-trimethoxyphenoxy)benzamide

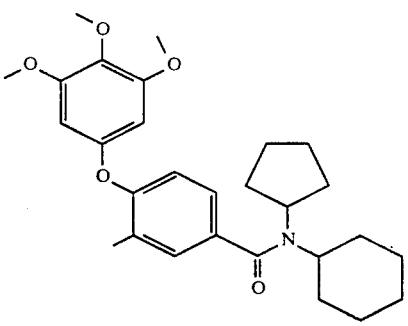

The reaction and workup were carried out in the same manner as described in Example 1 using 4-bromo-3-methyl benzoic acid N-cyclopentyl-N-cyclohexyl amide (983 mg, 2.7 mmol), 3,4,5-trimethoxy phenol (983 mg, 2.7 mmol) and cuprous oxide (200 mg, 1.3 mmol) in 2,4,6-collidine (15 ml). The crude product was chromatographed on silica gel using mixtures of ethyl acetate and hexane as eluents to give the title compound as a crystalline solid that could be recrystallized from ethyl acetate and hexane, m. pt. 181–182° C.

Anal Calcd. for $C_{28}H_{37}NO_5$: C, 71.92; H, 7.98; N, 3.00. Found: C, 71.79; H, 8.17; N, 2.96.

EXAMPLE 14

N-cyclohexyl-4-[hydroxy(3,4,5-trimethoxyphenyl)methyl]-N-(1-methylethyl)benzamide

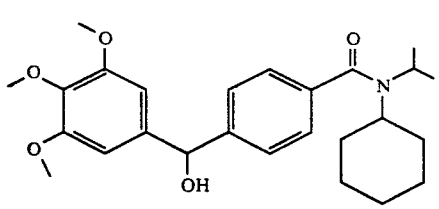

To a stirred, cold (−15° C.) solution of 3,4,5-trimethoxybromobenzene (965 mg, 3.9 mmol) in ethyl ether (15 ml) was added n-butyl lithium (3 ml of 1.6 M solution in hexane). The reaction mixture was stirred at −8° C. for 10 min., diluted with THF (5 ml) and warmed to 0° C. After stirring for 5 min., the reaction was cooled to −30° C. and a solution of terephthalaldehydic acid N-isopropyl-N-cyclohexyl amide (1.063 g, 3.9 mmol) in THF (5 ml) was added. After stirring at −30° C. for 10 min. and warming to room temperature, the reaction mixture was poured onto 0.5N $KHSO_4$ and extracted with ethyl acetate. The organic layer was washed with saturated NaCl solution and dried ($MgSO_4$). The drying agent was filtered and the filtrate concentrated in vacuo to give the crude product. This was chromatographed on silica gel using mixtures of ethyl acetate and hexane as eluents to give the title compound as a crystalline solid that could be recrystallized from cyclohexane containing a small amount of ethyl acetate, m. pt. 158-160° C.

Anal. Calcd. for $C_{26}H_{35}O_4N$: C, 70.72; H, 7.99; N, 3.17. Found: C, 70.74; H, 8.28; N, 3.19.

EXAMPLE 15

N-cyclohexyl-N-(1-methylethyl)-4-[(3,4,5-trimethoxyphenyl)methyl]benzamide

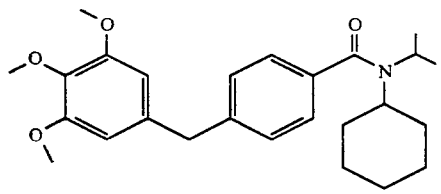

The compound prepared in Example 14 (800 mg, 1.81 mmol) in ethyl alcohol (20 mL) containing concentrated sulfuric acid (4 drops) was hydrogenated at 60 psi and room temperature using 5% Pd/C as catalyst. The catalyst was filtered and the filtrate concentrated in vacuo to give the crude product as an oil. The crude product was dissolved in ethyl acetate and washed twice with aqueous $NaHCO_3$ solution and then with saturated aqueous NaCl solution. After drying ($Na_2SO_4$), the organic layer was filtered and concentrated in vacuo to give the title compound.

Anal. Calcd. for $C_{26}H_{35}O_4N$: C, 73.37; H, 8.29; N, 3.29. Found: C, 73.34; H, 8.45; N, 3.24.

EXAMPLE 16

N-cyclohexyl-N-(1-methylethyl)-4-(3,4,5-trimethoxybenzoyl)benzamide

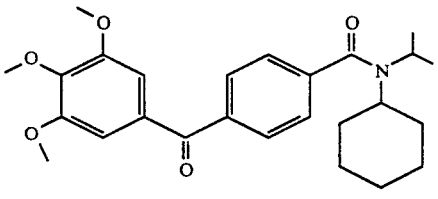

A solution of the compound prepared in Example 14 (500 mg, 1.1 mmol) in $CH_2Cl_2$ (5 ml) was added to a stirred slurry of pyridinium chlorochromate (500 mg, 2.3 mmol) and sodium acetate (180 mg, 2.2 mmol) in $CH_2Cl_2$ (10 ml). The reaction was stirred for 2 hrs at room temperature and diluted with ethyl ether (50 ml). After stirring the mixture for 15 min., the mixture was filtered through Florisil ® activated magnesium silicate (available from Aldrich Chemical Co., Milwaukee, Wisconsin, and the Florisil ® was washed thoroughly with ether. The filtrate was concentrated in vacuo and the residue chromatographed over silica gel using mixtures of ethyl acetate and hexane as the eluents. The title compound was obtained pure as a glass.

Anal. Calcd. for $C_{26}H_{33}NO_5$: C, 71.04; H, 7.57; N, 3.18. Found: C, 70.97; H, 7.60; N, 3.06.

EXAMPLE 17

N-cyclohexyl-N-cyclopentyl-4-[(2,4,5-trimethoxyphenyl)methyl]benzamide

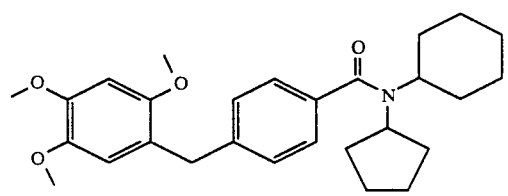

The carbinol prepared in Example 42 (1.0 g, 2.14 mmol) in EtOH (20 mL) was hydrogenated at 60 psi and room temperature using 5% Pd/C as catalyst. The catalyst was filtered and the filtrate was refiltered through Celite ® filter agent (available from Aldrich Chemical Co.). The filtrate was concentrated in vacuo and the residue was dissolved in ethyl acetate. The organic layer was washed with 5% $NaHCO_3$ solution and saturated NaCl solution and dried ($Na_2SO_4$). The drying agent was filtered and the filtrate concentrated in vacuo to give the crude product. Chromatography of the crude product on silica gel using mixtures of ethyl acetate and hexane as eluents gave the title compound as a glass.

Anal. Calcd. for $C_{28}H_{37}NO_4$: C, 74.26; H, 8.26; N, 3.10. Found: C, 73.82; H, 8.50; N, 3.10.

EXAMPLE 18

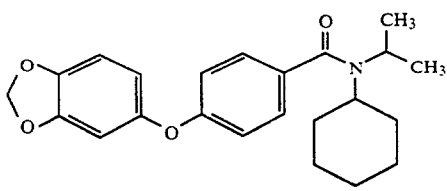

N-cyclohexyl-4-(3,4-methylenedioxyphenoxy)-N-(1-methylethyl)benzamide

The reaction was carried out in the same manner as described in Example 1 using p-bromobenzoic acid N-isopropyl-N-cyclohexyl amide (2.904 g, 8.96 mmol), 3,4-methylenedioxyphenol (1.354 g, 9.80 mmol) and cuprous oxide (641 mg, 4.48 mmol) in 2,4,6-collidine (15 ml). After 24 hr of refluxing, the reaction was cooled, diluted with ethyl acetate, and extracted with 0.5N HCl. A precipitate that formed on extraction was filtered and the aqueous filtrate was re-extracted with ethyl acetate. The organic layers were combined and washed three times with 6N HCl, twice with H₂O, three times with 5% NaOH, twice with H₂O and dried (Na₂SO₄) The drying agent was removed by filtration, and the filtrate concentrated in vacuo to give the crude product as a black oil. This was chromatographed on silica gel using mixtures of ethyl acetate and hexane as eluents to give the title compound as an oil.

Anal. Calcd. for $C_{23}H_{27}NO_4$: C, 72.42; H, 7.13; N, 3.67. Found: C, 72.25; H, 7.18; N, 3.61.

EXAMPLE 19

N-cyclohexyl-3-methoxy-N-(1-methylethyl)-4-(3,4,5-trimethoxyphenoxy)benzamide

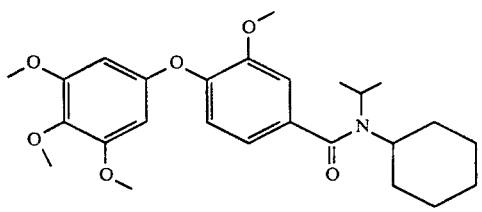

A slurry of cuprous oxide (1.00 g, 6.78 mmol) in a solution of 3,4,5-trimethoxyphenol (1.62 g, 8.53 mmol) and 4-bromo-3-methoxybenzoic acid N-isopropyl-N-cyclohexyl amide (2.42 g, 6.81 mmol) in 2,4,6-collidine (30 ml) was refluxed with stirring under a nitrogen atmosphere for 36 hr. Additional 3,4,5-trimethoxyphenol (0.32 g), and cuprous oxide (0.16 g) were added and reflux continued for 72 hrs. The reaction mixture was cooled, poured onto 6N HCl and extracted three times with ethyl acetate. The combined organic layers were washed twice with 5% NaOH solution, twice with saturated NaCl solution and dried (Na₂SO₄) The drying agent was filtered and the filtrate concentrated in vacuo to give 1.29 g of crude product. This material was chromatographed twice on silica gel using mixtures of ethyl acetate and hexane as the eluents to give the title compound as a crystalline solid that could be recrystallized from ethyl acetate hexane, m. pt. 126–128° C.

Anal. Calcd. for $C_{26}H_{35}NO_6$: C, 68.25; H, 7.71; N, 3.06. Found: C, 68.04; H, 7.88; N, 2.99.

EXAMPLE 20

N-cyclohexyl-4-[(2,4-dimethoxyphenoxy)methyl]-3-methoxy-N-(1-methylethyl)benzamide

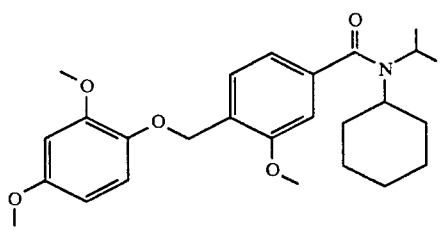

The phenoxide anion was prepared by reacting 2,4-dimethoxyphenol (1.00 g, 6.5 mmol) with sodium hydride (0.31 g of a 60% dispersion in oil, 7.75 mmol) in pyridine (12 ml) at 0°. After stirring for 10 min., CuBr.Me₂S (2.16 g, 10.4 mmol) Was added. After stirring for 20 min., 4-bromomethyl-3-methoxybenzoic acid N-isopropyl-N-cyclohexyl amide (3.65 g, 9.71 mmol) was added and the reaction mixture was stirred overnight at room temperature. The reaction mixture was poured onto saturated aqueous ammonium chloride solution (40 ml) and the aqueous layer was extracted three times with ethyl acetate. The combined organic layers were washed twice with 1N HCl, twice with saturated aqueous NaCl solution and dried (MgSO₄). The drying agent was filtered and the filtrate concentrated in vacuo to give the crude product as a black solid. This was chromatographed three times on silica gel using mixtures of ethyl acetate and hexane as eluents to give the title compound as a crystalline solid, m. pt. 98.5–101° C.

Anal. Calcd. for $C_{26}H_{35}NO_5$: C, 70.72; H, 7.99; N, 3.17. Found: C, 70.69; H, 8.10; N, 3.13.

EXAMPLE 21

N-cyclohexyl-3-methoxy-4-[(3-methoxyphenoxy)methyl]-N-(1-methylethyl)benzamide

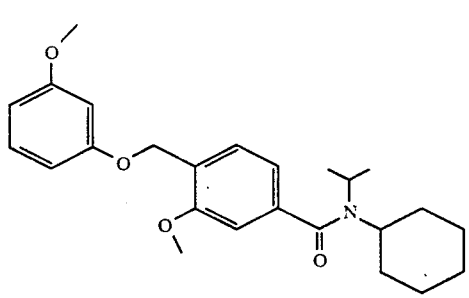

A slurry of K₂CO₃ (0.75 g, 5.43 mmol) in a solution of 4-bromomethyl-3-methoxybenzoic acid N-isopropyl-N-cyclohexyl amide (1.0 g, 2.7 mmol) and 3-methoxy phenol (0.35 g, 2.74 mmol) in dimethylformamide (DMF) (15 ml) was stirred overnight at room temperature. The reaction mixture was diluted with water (50 ml), extracted twice with ethyl acetate and dried (Na₂SO₄) The drying agent was filtered and the filtrate concentrated in vacuo to give the crude product as a dark oil. This material was purified by chromatography on silica gel using mixtures of ethyl acetate, CH₂Cl₂ and hexane as eluents to give the title compound as a glass.

Anal Calcd. for $C_{25}H_{33}NO_4$: C, 72.96; H, 8.08; N, 3.40. Found: C, 72.77; H, 8.19; N, 3.29.

EXAMPLE 22

N-cyclohexyl-4-[(3-methoxyphenoxy)methyl]-N-methylbenzamide

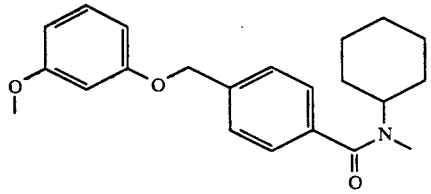

The reaction and workup were carried out in the same manner as for Example 21 using $K_2CO_3$ (674 mg, 4.88 mmol), 4-bromomethylbenzoic acid N-methyl-N-cyclohexyl amide (629 mg, 2.03 mmol) and 3-methoxyphenol (251 mg, 2.02 mmol). The crude product was chromatographed on silica gel using mixtures of ethyl acetate and hexane as eluents to give the title compound as a crystalline solid that could be recrystallized from ethyl acetate and hexane, m. pt. 90.38° C. (DSC).

Anal. Calcd. for $C_{22}H_{27}NO_3$: C, 74.76; H, 7.70; N, 3.96. Found: C, 74.51; H, 7.68; N, 3.93.

EXAMPLE 23

N-cyclohexyl-N-methyl-4-[(3,4,5-trimethoxyphenoxy)methyl]benzamide

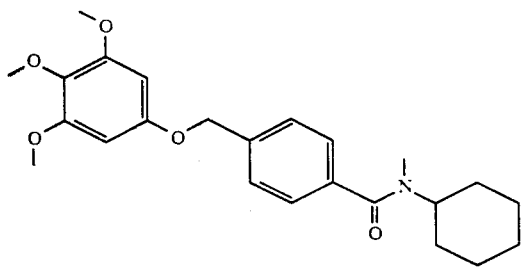

The reaction and workup were carried out in the same manner as for Example 21 using $K_2CO_3$ (576 mg, 4.17 mmol), 4-bromomethylbenzoic acid N-methyl-N-cyclohexyl amide (1.124 g, 3.62 mmol) and 3,4,5-trimethoxyphenol (648 mg, 3.52 mmol). The crude product was chromatographed on silica gel using mixtures of ethyl acetate and hexane as eluents to give the title compound as a crystalline solid that could be recrystallized from ethyl acetate and hexane, m. pt. 115.53° C. (DSC).

Anal. Calcd. for $C_{24}H_{31}NO_5$: C, 69.71; H, 7.56; N, 3.39. Found: C, 69.38; H, 7.55; N, 3.22.

EXAMPLE 24

4-bromo-N-cyclohexyl-N-isopropylbenzamide

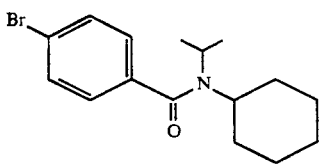

To a stirred, cold (0° C.) solution of 4-bromobenzoyl chloride (5.305 g, 24.2 mmol) in tetrahydrofuran (20 ml) was added dropwise a solution of isopropyl cylcohexyl amine (6.841 g, 48.4 mmol) in tetrahydrofuran (THF) (7ml). After stirring for 1 hr at 0° C., the reaction was stirred at room temperature for 3 hr. and refluxed for 3 hr. The reaction was concentrated in vacuo and the residual mass was dissolved in ethyl ether and water. The layers were separated and the organic layer washed once with water, twice with 0.5N HCl, once more with water, twice with 5% aqueous $NaHCO_3$ solution, and once with water. After drying over sodium sulfate, the organic layer was filtered, and the filtrate concentrated in vacuo to give the crude product. This material was purified by chromatography on silica el suing mixtures of EtOAc, and hexane as eluents to give the title compound.

EXAMPLE 25

4-bromomethyl-N-cyclohexyl-N-methylbenzamide

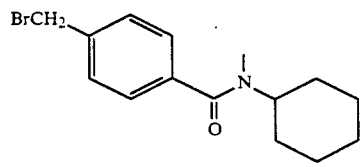

A solution of 4-bromomethylbenzoic acid (5.0 g, 23.3 mmol) in thionyl chloride (4.5 ml) was heated to reflux for 90 min. The clear, colorless reaction solution was diluted with toluene (50 ml) and concentrated in vacuo on the rotary evaporator. The residue was azeotroped once more with toluene to give 5.6 g of the acid chloride as a white solid.

To a cold (−10 °), stirred solution of the acid chloride (5.6 g) in tetrahydrofuran (50 ml) was added dropwise a solution of N-methylcyclohexylamine (5.73 g, 50.6 mmol) in tetrahydrofuran (35 ml). The reaction was stirred at 0° C. for 30 min. and at room temperature for 1 hr. The reaction was quenched by adding 1N HCl (100 ml) and diluted with ethyl acetate (50 ml). The layers were separated and the aqueous layer was washed three times with ethyl acetate. The combined organic layers were washed three times with saturated NaCl solution and dried ($Na_2SO_4$). The drying agent was filtered and the filtrate was concentrated in vacuo to give the title compound as an oil.

NMR ($CDCl_3$, ppm): 4.48 (2H, s, benzylic); 3.81 (3H, s, NMe); 0.80–1.93 (11H, hydrocarbon envelope); 7.15–7.5 (4H, phenyl).

EXAMPLE 26

4-bromo-N-cyclohexyl-N-cyclopentylbenzamide

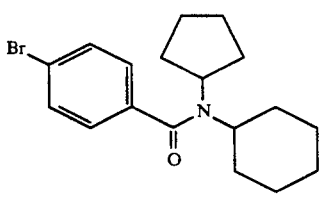

To a cold (+5° C.) stirred solution of N-cyclopentyl-N-cyclohexyl amine (4.0 g, 24 mmol) and triethylamine (2.5 g, 24 mmol) in tetrahydrofuran (50 ml) was added dropwise a solution of 4-bromobenzoyl chloride (5.0 g, 23 mmol) in tetrahydrofuran (20 ml). The reaction was stirred at room temperature overnight and worked up by diluting with water and ethyl acetate. The layers were separated and the organic layer was washed twice with 0.5N KHSO$_4$, twice with 5% NaHCO$_3$, and once with saturated aqueous NaCl solution. After drying over MgSO$_4$, the drying agent was filtered, the filtrate concentrated in vacuo, and the residue recrystallized from cyclohexane to give the title compound: m. p. 110–112° C.

Anal. Calcd. for C$_{18}$H$_{24}$BrNO: C, 61.72; H, 6.91; N, 4.00; Br, 22.81. Found: C, 61.51; H, 6.80; N, 3.85; Br, 22.52.

EXAMPLE 27

4-bromo-3-methyl-N-cyclohexyl-N-cyclopentylbenzamide

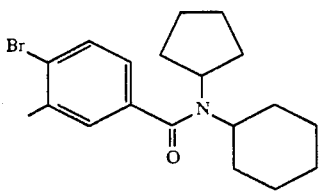

A solution of 4-bromo-3-methylbenzoic acid (25 g, 1.1 mol) in thionyl chloride (100 mL) was refluxed for 1 hr. The thionyl chloride was removed in vacuo, the residue azeotroped once with toluene and the crude product distilled to give 26 g (96%) of purified acid chloride (b. p. 85–86° at 0.7 Torr).

To a cold (0°) stirred solution of N-cyclohexyl-N-cyclopentyl amine (5.0 9, 30 mmol) and triethylamine (3.4 g, 34 mmol) in dry THF (60 mL) was added dropwise a solution of acid chloride (6.5 g, 30 mmol) in THF (20 mL). The reaction mixture was stirred overnight at room temperature and poured onto 0.5N KHSO$_4$ solution. The aqueous mixture was extracted with ethyl acetate, the combined organic layers were washed with 5% NaHCO$_3$ solution and saturated aqueous NaCl solution and dried (MgSO$_4$). The drying agent was filtered and the filtrate concentrated in vacuo to a crude solid. The solid was slurried in pentane, filtered and the filter cake further washed with pentane to give 9.8 g (90%) of product amide, m. p. 125–127° C.

Anal. Calcd. for C$_{19}$H$_{26}$BrNO: C, 62.64; H, 7.19; N, 3.84; Br, 21.93. Found: C, 62.54; H, 7.31; N, 3.71; Br, 21.59.

EXAMPLE 28

N-cyclohexyl-N-cyclopentyl-3-methyl-4-(3,4-methylenedioxyphenoxy)benzamide

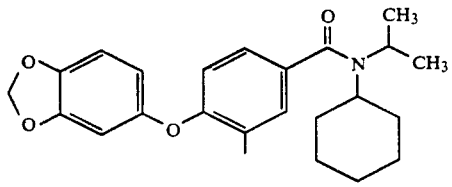

Starting with 4-bromo-3-methyl benzoic acid-N-isopropyl-N-cyclohexyl amide and 3,4-methylenedioxyphenol and following the procedure described in Example 18 gives the title compound.

EXAMPLE 29

4-(N,N-dicyclopentylcarboxamido)benzaldehyde

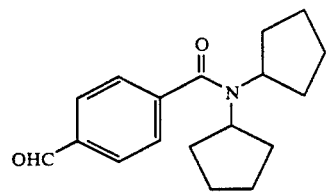

A solution of 4-carboxybenzaldehyde (7.0 g, 46.5 mmol), thionyl chloride (3.5 mL), and dimethylformamide (0.34 mL) in benzene (250 mL) was refluxed for 6 hr. The reaction mixture was concentrated in vacuo and azeotroped (twice) with benzene. The resultant crude brown solid was dissolved in THF (120 mL) and cooled to −5° C. A solution of dicyclopentylamine (14.3 g, 93.1 mmol) in THF (80 mL) was added dropwise over 15 minutes. The reaction was stirred at room temperature for 15 min. The reaction was quenched with water (150 mL), 0.07 N NaOH (375 mL) was added and the aqueous solution extracted four times with ethyl acetate. The combined organic layers were washed three times with water and dried (Na$_2$SO$_4$). The drying agent was filtered and the filtrate concentrated in vacuo to give the crude amide suitable for use in the synthesis of Example 10.

EXAMPLE 30

4-(N-cyclohexyl-N-cyclopentylcarboxamido)benzaldehyde

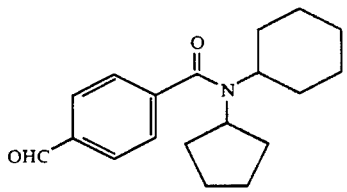

The acid chloride of 4-carboxybenzaldehyde (7.0 g, 46.5 mmol) was prepared in the same manner as in Example 29 using thionyl chloride (3.5 mL) and dimethylformamide (0.34 mL) in benzene (250 mL). The amide was prepared from the acid chloride in the same manner and using the same workup procedure as in Example 29 using N-cyclohexyl-N-cyclopentyl amine (15.6 g, 93.1 mmol) in THF (150 mL) at 0° C. The crude product was suitable for use without further purification.

Anal. Calcd. for C$_{19}$H$_{25}$O$_2$N: C, 76.22; H, 8.42; N, 4.68. Found: C, 76.00; H, 8.43; N, 4.69.

EXAMPLE 31

4-(N-isopropyl-N-cyclohexylcarboxamido)benzaldehyde

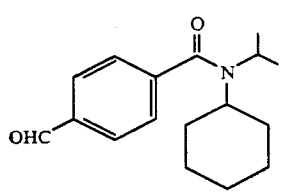

The acid chloride of 4-carboxybenzaldehyde (7.0 g, 46.5 mmol) was prepared in the same manner as in Example 29 using thionyl chloride (3.5 mL) and dimethylformamide (0.34 mL) in benzene (250 mL). The amide was prepared from the acid chloride in the same manner and using the same workup procedure as in Example 29 using N-isopropyl-N-cyclohexyl amine (13.3 g, 93.1mmol) in THF (150 mL) at 0° C. The crude product was suitable for use without further purification.

Anal. Calcd. for $C_{17}H_{23}O_2N$: C, 74.69; H, 8.48; N, 5.12. Found: C, 74.32; H, 8.56; N, 5.06.

EXAMPLE 32

4-bromo-3-methoxybenzoic acid N-isopropyl-N-cyclohexyl amide

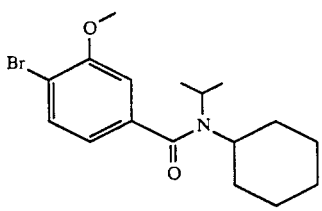

A solution of 4-bromo-3-methoxybenzoic acid (2.80 g, 12.1 mmol) in thionyl chloride (30 mL) was refluxed for 3 hr. The reaction was concentrated in vacuo and the residue azeotroped three times with toluene. A solution of the resulting crude solid (3.11 g, 8.75 mmol) in THF (10 mL) was added to a stirred, cold (0° C.) solution of N-isopropylcyclohexyl amine (1.7 g, 11.7 mmol) and triethylamine (1.20 g, 11.7 mmol) in THF (10 mL). The reaction was stirred at room temperature overnight. The reaction was filtered and the filtrate diluted with ethyl acetate and washed three times with 1N HCl, three times with saturated NaHCO₃, three times with saturated NaCl solution and dried (Na₂SO₄). The drying agent was filtered and the filtrate concentrated in vacuo to give a dark brown oil. The oil was purified by chromatography on silica gel using mixtures of ethyl acetate and hexane as eluents. This yielded crystalline amide, m. p. 104–107° C.

EXAMPLE 33

N-cyclohexyl-N-(1-methylethyl)-4-(3,4,5-trimethoxyphenylamino)benzamide

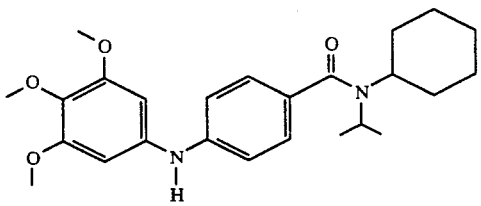

A slurry of cuprous oxide (300 mg, 2.1 mmol) in a solution of 3,4,5-trimethoxyaniline (733 mg, 4.0 mmol) and p-bromobenzoic acid N-isopropyl-N-cyclohexyl amide (1.290 g, 3.98 mmol) in 2,4,6-collidine (20 ml) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried (Na₂SC₄). The drying agent is filtered and the filtrate concentrated in vacuo to give the crude product. This material is chromatographed on silica gel using mixtures of methanol, methylene chloride and ammonium hydroxide as the eluents to give the title compound.

EXAMPLE 34

4-bromobenzoic acid N-n-hexyl-N-cyclohexyl amide

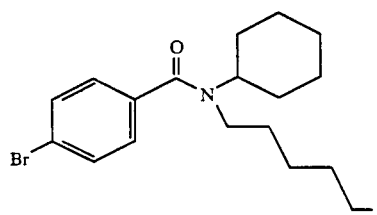

To a cold (0° C. to 5° C.) stirred solution of N-n-hexyl-N-cyclohexyl amine (4.40 g, 24 mmol) and triethylamine (2.5 g, 24 mmol) in dry THF (50 mL) is added dropwise a solution of acid chloride (5.0 g, 23 mmol) in THF (20 mL). The reaction is stirred at room temperature overnight and worked up in the same manner as for 4-bromo-3-methylbenzoic acid N-cyclopentyl-N-cyclohexyl amide. The crude product is purified by either recrystallization or by chromatography on silica gel using mixtures of ethyl acetate and hexane as eluents.

EXAMPLE 35

4-bromobenzoic acid N-tert-butyl-N-cyclohexyl amide

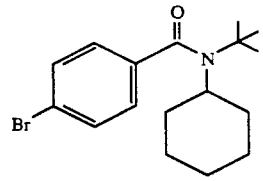

To a cold (0° C. to 5° C.) stirred solution of N-tertbutyl-N-cyclohexyl amine (3.73 g, 24 mmol) and triethylamine (2.5 g, 24 mmol) in dry THF (50 mL) is added dropwise a solution of acid chloride (5.0 g, 23 mmol) in THF (20 mL). The reaction is stirred at room temperature overnight and worked up in the same manner as for 4-bromo-3-methylbenzoic acid N-cyclopentyl-N-cyclohexyl amide. The crude product is purified by either recrystallization or by chromatography on silica gel using mixtures of ethyl acetate and hexane as eluents.

EXAMPLE 36

N-cyclohexyl-N-(1,1-dimethylethyl)-4-(3,4,5-trimethoxyphenoxy)benzamide

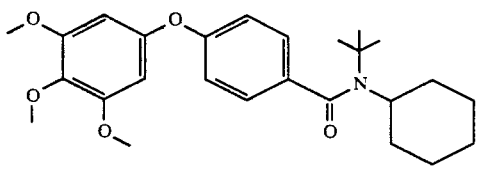

A slurry of cuprous oxide (300 mg, 2.1 mmol) in a solution of 3,4,5-trimethoxyphenol (736 mg, 4.0 mmol) and p-bromobenzoic acid N-tert-butyl-N-cyclohexyl amide (1.35 g, 4.0 mmol) 2,4,6-collidine (20 ml) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried ($Na_2SO_4$). The drying agent is filtered and the filtrate concentrated in vacuo to give the crude product. This material is chromatographed on silica gel using mixtures of ethyl acetate and hexane as the eluents to give the title compound.

EXAMPLE 37

N-cyclohexyl-N-(n-hexyl)-4-(3,4,5-trimethoxyphenoxy)benzamide

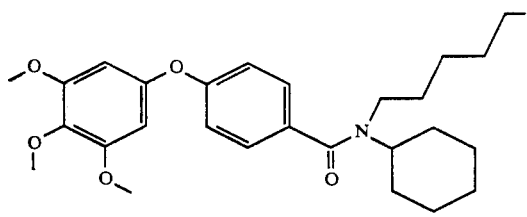

A slurry of cuprous oxide (300 mg, 2.1 mmol) in a solution of 3,4,5-trimethoxyphenol (736 mg, 4.0 mmol) and p-bromobenzoic acid N-n-hexyl-N-cyclohexyl amide (1.47 g, 4.0 mmol) in 2,4,6-collidine (20 ml) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried ($Na_2SO_4$). The drying agent is filtered and the filtrate concentrated in vacuo to give the crude product. This material is chromatographed on silica gel using mixtures of ethyl acetate and hexane as the eluents to give the title compound.

EXAMPLE 38

N-cyclohexyl-4-(4-ethoxyphenoxy)-N-(1-methylethyl)-benzamide

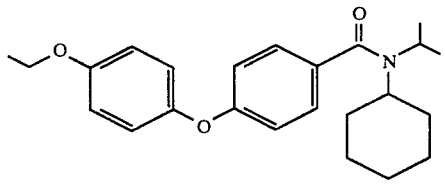

The reaction and workup are carried out in the same manner as described for Example 1 using p-bromobenzoic acid N-isopropyl-N-cyclohexyl amide (1.75g, 5.40 mmol), 4-ethoxy phenol (796 mg, 5.76 mmol) and cuprous oxide (390 mg, 2.73 mmol) in collidine (15 ml). The crude product is chromatographed on silica gel using mixtures of ethyl acetate and hexane as eluents to give the title compound.

EXAMPLE 39

N-cyclohexyl-4-[hydroxy(3,4-methylenedioxyphenyl)methyl]-N-(1-methylethyl)benzamide

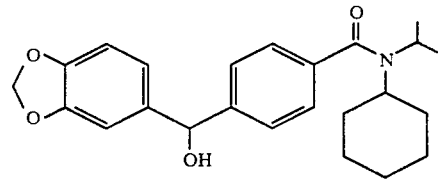

To a stirred solution of 4-bromo-1,2-(methylenedioxy)benzene (1.00 g, 6.0 mmol) in ethyl ether (30 mL) at 0° under an argon atmosphere is added n-BuLi (3.75 mL of 1.6 M solution in hexane). Tetrahydrofuran (10 mL) is added. The reaction mixture is cooled to −20° C. and a solution of terephthalaldehydic acid N-isopropyl-N-cyclohexyl amide (0.82 g, 3.0 mmol) in THF: ethyl ether (4:3, 35 mL) is added rapidly. The reaction is followed by thin layer chromatography until complete. The reaction is quenched at −15° C. by adding water (50 mL) and 1N HCl(20 mL). The reaction is further diluted with water (300 mL) and extracted three times with EtOAc (50 mL portions). The combined extracts are washed twice with saturated NaCl solution and dried ($MgSO_4$). The drying agent is filtered and the filtrate concentrated in vacuo to give the crude product. The crude product is chromatographed on silica gel using mixtures of ethyl acetate and hexane as eluents to give the title compound.

EXAMPLE 40

N-cyclohexyl-N-(1-methylethyl)-4-[(3,4-methylenedimethoxyphenyl)methyl]benzamide

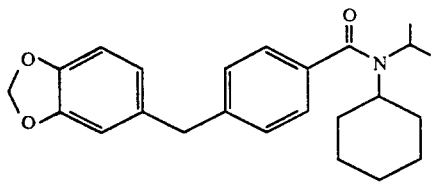

The alcohol from Example 39 (0.332 g, 0.84 mmol) in EtOH (20 mL) containing concentrated sulfuric acid (2 drops) is hydrogenated at 60 psi and room temperature using 5% Pd/C as catalyst. The catalyst is filtered and the filtrate concentrated in vacuo to give the crude product as an oil. The crude product is dissolved in ethyl acetate and washed twice with aqueous $NaHO_3$ solution and then with saturated aqueous NaCl solution. After drying ($Na_2SO_4$) the organic layer is filtered and concentrated in vacuo. Chromatography of the residue on silica gel using mixtures of ethyl acetate and hexane as eluents gives the title compound.

EXAMPLE 41

N-cyclohexyl-N-(1-methylethyl)-4-(3,4-methylenedioxyoxybenzoyl)benzamide

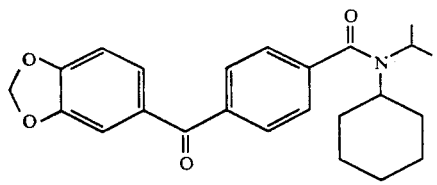

A solution of the alcohol from Example 39 (435 mg, 1.1 mmol) in $CH_2Cl_2$ (5 ml) is added to a stirred slurry of pyridinium chlorochromate (500 mg, 2.3 mmol) and NaOAC (180 mg, 2.2 mmol) in $CH_2Cl_2$ (10 ml). The reaction is stirred at room temperature and followed by thin layer chromatography until complete. The reaction is diluted with ethyl ether (50 ml). After stirring the mixture for 15 min., the mixture is filtered through Florisil ® activated magnesium silicate and the Florisil ® washed thoroughly with ether. The filtrate is concentrated in vacuo and the residue chromatographed over silica gel using mixtures of ethyl acetate and hexane as the eluents to give the title compound.

EXAMPLE 42

N-cyclohexyl-N-cyclopentyl-4-[hydroxy(2,4,5-trimethoxyphenyl)methyl]benzamide

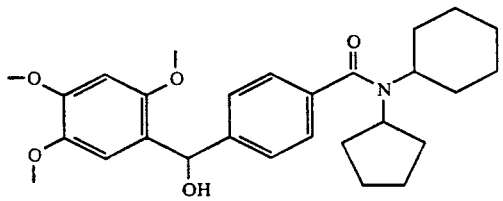

To a cold (−70° C.), stirred solution of 4-bromo-N-cyclohexyl-N-cyclopentylbenzamide (1.5 g, 4.3 mmol) in THF (20 ml) was added slowly a solution of tert-butyllithium (5 ml of 1.7 M solution in pentane) under an Argon atmosphere. The reaction was stirred at −70° to −75° for 20 min. and a solution of 2,4,5-trimethoxybenzaldehyde (843 mg, 4.3 mmol) in THF (10 ml) was added dropwise over 30 min. The reaction was stirred at −70° to −75° for 30 min. and at room temperature for 1 hr. The reaction was quenched by the addition of water and the aqueous layer extracted three times with ethyl acetate. The combined organic layers were washed with water and dried ($Na_2SO_4$). The drying agent was filtered and the filtrate concentrated in vacuo to give the crude product. Purification was effected by chromatography on silica gel using mixtures of ethyl acetate and hexane. The product was isolated as a glass.

Anal Calcd for $C_{28}H_{37}NO_5$: C, 71.51; H, 7.53; N, 2.99. Found: C, 71.23; H, 7.33; H, 2.99.

EXAMPLE 43

N-cyclohexyl-3-ethoxy-N-(1-methylethyl)-4-(3,4,5-trimethoxyphenoxy)benzamide

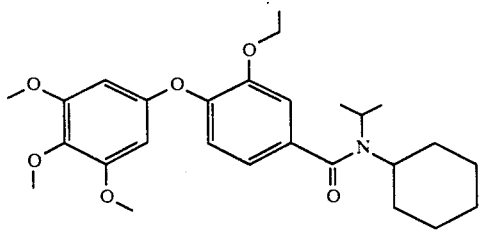

A slurry of cuprous oxide (300 mg, 2.1 mmol) in a solution of 3,4,5-trimethoxyphenol (736 mg, 4.0 mmol) and 4-bromo-3-ethoxybenzoic acid N-isopropyl-N-cyclohexyl amide (1.47 g, 4.0 mmol) in 2,4,6-collidine (20 ml) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried ($Na_2SO_4$). The drying agent is filtered and the filtrate concentrated in vacuo to give the crude product. This material is chromatographed on silica gel using mixtures of ethyl acetate and hexane as the eluents to give the title compound.

EXAMPLE 44

N-cyclohexyl-N-(1-methylethyl)-4-(3,4,5-triethoxyphenoxy)benzamide

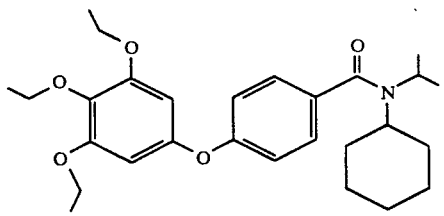

A slurry of cuprous oxide (300 mg, 2.1 mmol) in a solution of 3,4,5-triethoxyphenol (777 mg, 4.0 mmol) and p-bromobenzoic acid N-isopropyl-N-cyclohexyl amide (1.30 g, 4.0 mmol) in 2,4,6-collidine (20 ml) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried (Na₂SO₄). The drying agent is filtered and the filtrate concentrated in vacuo to give the crude product. This material is chromatographed on silica gel using mixtures of ethyl acetate and hexane as the eluents to give the title compound.

EXAMPLE 45

N-cyclohexyl-4-[hydroxy(3,4,5-trimethoxyphenyl)methyl]-3-methoxy-N-(1-methylethyl)benzamide

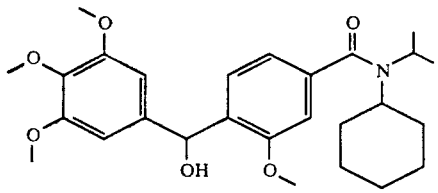

To a stirred, cold (−15°) solution of 3,4,5-trimethoxybromobenzene (965 mg, 3.9 mmol) in ethyl ether (15 ml) is added n-BuLi (3 ml of 1.6 M solution in hexane). The reaction mixture is stirred at −8° C. for 10 min., diluted with THF (5 ml) and warmed to 0° C. After stirring for 5 min., the reaction is cooled to −30° C. and a solution of 4-formyl-3-methoxybenzoic acid N-isopropyl-N-cyclohexyl amide (1.18 g, 3.9 mmol) in THF (5 ml) is added. After stirring at −30° C. for 10 min. and warming to room temperature, the reaction is poured onto 0.5 N KHSO₄ and extracted with ethyl acetate. The organic layer is washed with saturated NaCl solution and dried (MgSO₄). The drying agent is filtered and the filtrate concentrated in vacuo to give the crude product. This is chromatographed on silica gel using mixtures of ethyl acetate and hexane as eluents to give the title compound.

EXAMPLE 46

N-cyclohexyl-3-methoxy-N-(1-methylethyl)-4-[(3,4,5-trimethoxyphenyl)methyl]benzamide

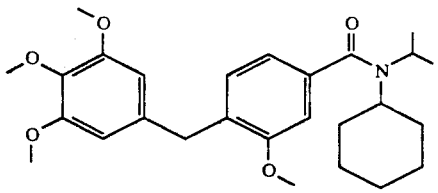

The compound of Example 45 (800 mg, 1.81 mmol) in EtOH (20 mL) containing concentrated sulfuric acid (4 drops) is hydrogenated at 60 psi and room temperature using 5% Pd/C as catalyst. The catalyst is filtered and the filtrate concentrated in vacuo to give the crude product. The crude product is dissolved in ethyl acetate and washed twice with aqueous NaHO₃ solution and then with saturated aqueous NaCl solution. After drying (Na₂SO₄) the organic layer is filtered and concentrated in vacuo. Purification to give the title compound is carried out by chromatography of the residue on silica gel using mixtures of ethyl acetate and hexane as the eluents.

EXAMPLE 47

N-cyclohexyl-4-[hydroxy(3,4,5-trimethoxyphenyl)methyl]-3-methyl-N-(1-methylethyl)benzamide

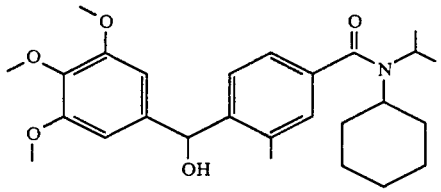

To a stirred, cold (−15° C.) solution Of 3,4,5-trimethoxybromobenzene (965 mg, 3.9 mmol) in ethyl ether (15 ml) is added n-BuLi (3 ml of 1.6 M solution in hexane). The reaction mixture is stirred at −8° C. for 10 min., diluted with THF (5 ml) and warmed to 0° C. After stirring for 5 min., the reaction is cooled to −30° C. and a solution of 4-formyl-3-methylbenzoic acid N-isopropyl-N-cyclohexyl amide (1.12 g, 3.9 mmol) in THF (5 ml) is added. After stirring at −30° C. for 10 min. and warming to room temperature, the reaction is poured onto 0.5 N KHSO₄ and extracted with ethyl acetate. The organic layer is washed with saturated NaCl solution and dried (MgSO₄). The drying agent is filtered and the filtrate concentrated in vacuo to give the crude product. This is chromatographed on silica gel using mixtures of ethyl acetate and hexane as eluents to give the title compound.

EXAMPLE 48

N-cyclohexyl-3-methyl-N-(1-methylethyl)-4-[(3,4,5-trimethoxyphenyl)methyl]benzamide

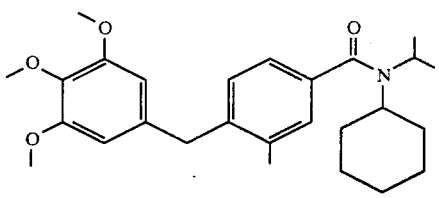

The compound of Example 47 (800 mg, 1.81 mmol) in EtOH (20 mL) containing concentrated sulfuric acid (4 drops) is hydrogenated at 60 psi and room temperature using 5% Pd/C as catalyst. The catalyst is filtered and the filtrate concentrated in vacuo to give the crude product. The crude product is dissolved in ethyl acetate and washed twice with aqueous NaHO₃ solution and then with saturated aqueous NaCl solution. After drying (Na₂SO₄) the organic layer is filtered and concentrated in vacuo. Purification to give the title compound is carried out by chromatography of the residue on silica gel using mixtures of ethyl acetate and hexane as the eluents.

EXAMPLE 49

4-bromo-3-chloro-N-cyclohexyl-N-isopropylbenzamide

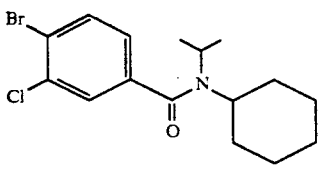

A solution of 4-bromo-3-chlorobenzoic acid (23.5 g, 0.1 mmol) in thionyl chloride (100 mL) is refluxed for 1 hr. The thionyl chloride is removed in vacuo, the residue azeotroped once with toluene and the crude product distilled to give the purified acid chloride.

To a stirred, cold (0° C.) solution of 4-bromo-3-chlorobenzoyl chloride (6.14 g, 24.2 mmol) in tetrahydrofuran (20 ml) is added dropwise a solution of isopropyl cyclohexyl amine (6.841g, 48.4 mmol) in THF (7 mL). After stirring for 1 hr. at 0° C., the reaction is stirred at room temperature for 3 hr. and refluxed for 3 hr. The reaction is concentrated in vacuo and the residual mass is dissolved in ethyl ether and water. The layers are separated and the organic layer washed once with water, twice with 0.5N HCl, once more with water, twice with 5% aqueous $NaHO_3$ solution, and once with water. After drying over sodium sulfate, the organic layer is filtered, and the filtrate concentrated in vacuo to give the crude product. This material is purified by chromatography on silica gel using mixtures of EtOAc, and hexane as eluents to give the title compound.

EXAMPLE 50

3-chloro-N-cyclohexyl-N-(1-methylethyl)-4-(3,4,5-trimethoxyphenoxy)benzamide

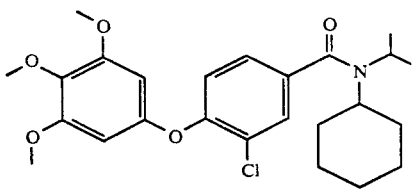

A slurry of cuprous oxide (300 mg, 2.1 mmol) in a solution of 3,4,5-trimethoxyphenol (736 mg, 4.0 mmol) and 4-bromo-3-chloro-N-cyclohexyl-N-isopropylbenzamide (1.43 g, 4.0 mmol) in 2,4,6-collidine (20 mL) is refluxed with stirring under a nitrogen atmosphere for 18 hr. The reaction is cooled, poured onto dilute aqueous HCl and extracted three times with ethyl acetate. The combined organic layers are washed twice with saturated aqueous NaCl solution, twice with 5% NaOH solution, twice with saturated NaCl solution and dried ($Na_2SO_4$). The drying agent is filtered and the filtrate concentrated in vacuo to give the crude product. This material is chromatographed on silica gel using mixtures of ethyl acetate and hexane as the eluents to give the title compound.

EXAMPLE 51

2-bromo-4-(N-isopropyl-N-cyclohexylcarboxamido)benzaldehyde

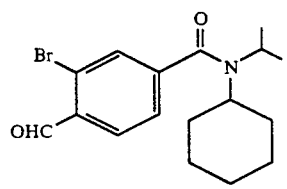

A solution of 4-carboxy-2-bromobenzaldehyde (10.7 g, 46.5 mmol), thionyl chloride (3.5 mL), and dimethylformamide (0.34 mL) in benzene (250 mL) is refluxed for 6 hr. The reaction mixture is concentrated in vacuo and azeotroped (twice) with benzene. The resultant crude brown solid is dissolved in THF (120 mL) and cooled to −5° C. A solution of N-isopropylcyclohexyl amine (13.2 g, 93.1 mmol) in THF (80 mL) is added dropwise over 15 minutes. The reaction is stirred at room temperature for 15 min. The reaction is quenched with water (150 mL) and 0.07 N NaOH (375 mL) is added and the aqueous solution extracted four times with ethyl acetate. The combined organic layers are washed three times with water and dried ($Na_2SO_4$). The drying agent is filtered and the filtrate concentrated in vacuo to give the amide.

EXAMPLE 52

3-bromo-N-cyclohexyl-4-[hydroxy(3,4,5-trimethoxyphenyl) methyl]-N-(1-methylethyl)benzamide

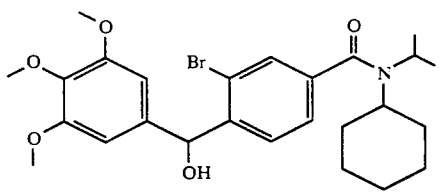

To a stirred, cold (−15° C.) solution of 3,4,5-trimethoxybromobenzene (965 mg, 3.9 mmol) in ethyl ether (15 mL) is added n-BuLi (3 mL of 1.6 M solution in hexane). The reaction mixture is stirred at −8° C. for 10 min., diluted with THF (5 mL) and warmed to 0° C. After stirring for 5 min., the reaction is cooled to −30° C. and a solution of 2-bromo-4-(N-isopropyl-N-cyclohexylcarboxamido)benzaldehyde (1.37 g, 3.9 mmol) in THF (5 mL) is added. After stirring at −30° C. for 10 min. and warming to room temperature, the reaction is poured onto 0.5N $KHSO_4$ and extracted with ethyl acetate. The organic layer is washed with saturated NaCl solution and dried ($MgSO_4$). The drying agent is filtered and the filtrate concentrated in vacuo to give the crude product. This is chromatographed on silica gel using mixtures of ethyl acetate and hexane as eluents to give the title compound.

EXAMPLE 53

3-bromo-N-cyclohexyl-N-(1-methylethyl)-4-(3,4,5-trimethoxyphenoxy)benzamide

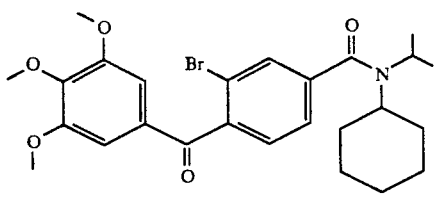

A solution of alcohol from Example 52 (573 mg, 1.1 mmol) in CH₂Cl₂ (5 mL) is added to a stirred slurry of pyridinium chlorochromate (500 mg, 2.3 mmol) and NaOAC (180 mg, 2.2 mmol) in CH₂Cl₂ (10 mL). The reaction is stirred for 2 hrs. at room temperature and diluted with ethyl ether (50 mL). After stirring the mixture for 15 min., the mixture is filtered through Florisil ® activated magnesium silicate and the Florisil ® washed thoroughly with ether. The filtrate is concentrated in vacuo and the residue chromatographed over silica gel using mixtures of ethyl acetate and hexane as eluents to give the title compound.

What is claimed is:

1. A compound of the formula:

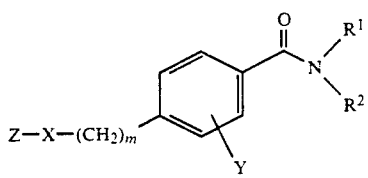

or a pharmaceutically acceptable salt thereof, wherein Z is

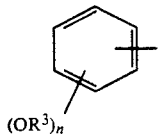

wherein $R^3$ is alkyl having 1 to 6 carbon atoms and, when n is greater than 1, each $R^3$ can be the same or different; and n is an integer from 1 to 3;

$R^1$ and $R^2$ can each independently be hydrogen, straight or branched chain alkyl of 1 to 10 carbon atoms, or cycloalkyl having 3 to 8 carbon atoms which can optionally be substituted at one or more positions by alkyl of 1 to 6 carbon atoms;

X is oxygen, sulfur, $NR^4$, wherein $R^4$ is hydrogen or alkyl having 1 to 4 carbon atoms, C=O, CHOH, or CH₂;

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms; and m is an integer from 0 to 3; with the proviso that when X is oxygen or CH₂ and m is 1, $R^1$ and/or $R^2$ is cycloalkyl.

2. A compound according to claim 1 of the formula

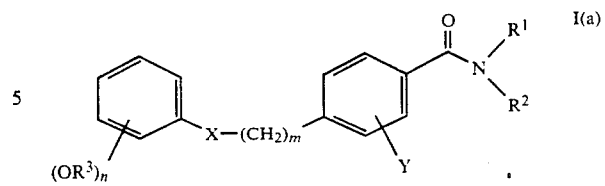

or a pharmaceutically acceptable salt thereof, wherein $R^1$ and $R^2$ can each independently be hydrogen, straight or branched chain alkyl of 1 to 10 carbon atoms, or cycloalkyl having 3 to 8 carbon atoms which can optionally be substituted at one or more positions by alkyl of 1 to 6 carbon atoms;

X is oxygen, sulfur, $NR^4$, wherein $R^4$ is hydrogen or alkyl having 1 to 4 carbon atoms, C=O, CHOH, or CH₂;

Y is hydrogen; alkoxy having 1 to 6 carbon atoms; halogen, wherein the halogen is selected from the group consisting of bromo, fluoro, and chloro; or straight or branched chain alkyl having 1 to 6 carbon atoms;

n is an integer from 1 to 3;

m is an integer from 0 to 3; and $R^3$ is alkyl having 1 to 6 carbon atoms and, when n is greater than 1, each $R^3$ can be the same or different; with the proviso that when X is oxygen or CH₂ and m is 1, $R^1$ and/or $R^2$ is cycloalkyl.

3. A compound according to claim 1 of the formula

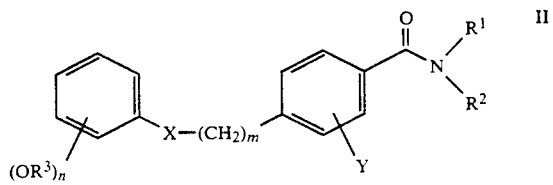

wherein $R^1$ and $R^2$ are each independently selected from straight or branched chain alkyl having 1 to 6 carbon atoms; or cycloalkyl having 3 to 8 carbon atoms which can optionally be substituted at one or more positions by alkyl of 1 to 6 carbon atoms;

Y is hydrogen; alkoxy having 1 to 4 carbon atoms; halogen, wherein the halogen is selected from the group consisting of bromo, fluoro, or chloro; straight or branched chain alkyl having 1 to 6 carbon atoms;

X is oxygen, C=O, CHOH, or CH₂;

n is an integer from 1 to 3;

m is an integer from 0 to 3; and $R_3$ is alkyl having 1 to 4 carbon atoms and, wherein n is greater than 1, each $R^3$ can be the same or different; with the proviso that when X is oxygen or CH₂ and m is 1, $R^1$ and/or $R^2$ is cycloalkyl.

4. A compound of the formula

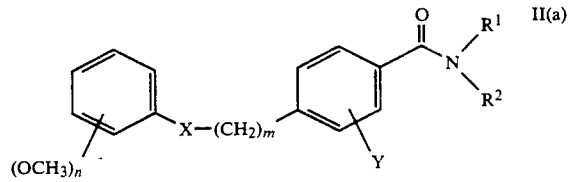

wherein
R¹ and R² are each independently selected from straight or branched chain alkyl having 1 to 6 carbon atoms or cycloalkyl having 4 to 6 carbon atoms;
Y is hydrogen; alkyoxy having 1 to 4 carbon atoms; or alkyl having 1 to 4 carbon atoms;
X is oxygen, C=O, CHOH, or CH$_2$;
n is an integer from 1 to 3; and
m is 0 or 1.

5. A compound according to claim 2 which is N-cyclohexyl-N-(1-methylethyl)-4-(3,4,5-trimethoxyphenoxy)benzamide.

6. A compound according to claim 2 which is N-cyclohexyl-4-(4-methoxyphenoxy)-N-(1-methylethyl)-benzamide.

7. A compound according to claim 2 which is N-cyclohexyl-4-(3-methoxyphenoxy)-N-(1-methylethyl)-benzamide.

8. A compound according to claim 2 which is N-cyclohexyl-N-cyclopentyl-4-(3,4,5-trimethoxyphenoxy)benzamide.

9. A compound according to claim 2 which is N-cyclohexyl-N-cyclopentyl-4-(3,4-dimethoxyphenoxy)-benzamide.

10. A compound according to claim 2 which is N-cyclohexyl-4-(3,4-dimethoxyphenoxy)-N-(1-methylethyl)benzamide.

11. A compound according to claim 2 which is N,N-dicyclopentyl-4-(3,4-dimethoxyphenoxy)benzamide.

12. A compound according to claim 2 which is N-cyclohexyl-4-[(3,4-dimethoxyphenyl)hydroxymethyl]-N-(1-methylethyl) benzamide.

13. A compound according to claim 2 which is N-cyclohexyl-N-cyclopentyl-4-[(3,4-dimethoxyphenyl)-hydroxymethyl]benzamide.

14. A compound according to claim 2 which is N,N-dicyclopentyl-4-[(3,4-dimethoxyphenyl)hydroxymethyl]benzamide.

15. A compound according to claim 2 which is N,N-dicyclopentyl-4-[(3,4-dimethoxyphenyl)methyl]benzamide.

16. A compound according to claim 2 which is N-cyclohexyl-4-(3,5-dimethoxyphenoxy)-N-(1-methylethyl)benzamide.

17. A compound according to claim 2 which is N-cyclohexyl-N-cyclopentyl-3-methyl-4-(3,4,5-trimethoxyphenoxy)benzamide.

18. A compound according to claim 2 which is N-cyclohexyl-4-[hydroxy(3,4,5-trimethoxyphenyl)methyl]-N-(1-methylethyl) benzamide.

19. A compound according to claim 2 which is N-cyclohexyl-N-(1-methylethyl)-4-[(3,4,5-trimethoxyphenyl)methyl]benzamide.

20. A compound according to claim 2 which is N-cyclohexyl-N-(1-methylethyl)-4-(3,4,5-trimethoxybenzoyl)benzamide.

21. A compound according to claim 2 which is N-cyclohexyl-N-cyclopentyl-4-[(2,4,5-trimethoxyphenyl)-methyl]benzamide.

22. A compound according to claim 2 which is N-cyclohexyl-3-methoxy-N-(1-methylethyl)-4-(3,4,5-trimethoxyphenoxy) benzamide.

23. A compound according to claim 2 which is N-cyclohexyl-4-[(2,4-dimethoxyphenoxy)methyl]-3-methoxy-N-(1-methylethyl)benzamide.

24. A compound according to claim 2 which is N-cyclohexyl-3-methoxy-4-[(3-methoxyphenoxy)methyl]-N-(1-methylethyl)benzamide.

25. A compound according to claim 2 which is N-cyclohexyl-4-[(3-methoxyphenoxy)methyl]-N-methylbenzamide.

26. A compound according to claim 2 which is N-cyclohexyl-N-methyl-4-[(3,4,5-trimethoxyphenoxy)methyl]benzamide.

27. A pharmaceutical composition for use in the treatment of diseases or disorders mediated by platelet-activating factor comprising a therapeutically effective amount of a compound of the formula

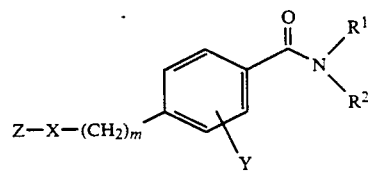

or a pharmaceutically acceptable salt thereof, wherein Z is

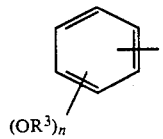

wherein R³ is alkyl having 1 to 6 carbon atoms and, when n is greater than 1, each R³ can be the same or different; and n is an integer from 1 to 3;
R¹ and R² can each independently by hydrogen, straight or branched chain alkyl of 1 to 10 carbon atoms, or cycloalkyl having 3 to 8 carbon atoms which can optionally be substituted at one or more positions by alkyl of 1 to 6 carbon atoms;
X is oxygen, sulfur, NR⁴, wherein R⁴ is hydrogen or alkyl having 1 to 4 carbon atoms, C=O, CHOH, or CH$_2$;
Y is hydrogen, alkoxy having 1 to 6 carbon atoms; halogen, wherein the halogen is selected from the group consisting of bromo, fluoro, and chloro; straight or branched chain alkyl having 1 to 6 carbon atoms; and
m is an integer from 0 to 3; with the proviso that when X is oxygen or CH$_2$ and m is 1, R¹ and/or R² is cycloalkyl;
and a pharmaceutically acceptable carrier.

28. A pharmaceutical composition according to claim 27 for use in the treatment of diseases or disorders mediated by platelet-activating factor comprising a therapeutically effective amount of a compound selected from the group consisting of
N-cyclohexyl-N-(1-methylethyl)-4-(3,4,5-trimethoxyphenoxy)-benzamide;
N-cyclohexyl-4-(4-methoxyphenoxy)-N-(1-methylethyl)benzamide;
N-cyclohexyl-4-(3-methoxyphenoxy)-N-(1-methylethyl)benzamide;
N-cyclohexyl-N-cyclopentyl-4-(3,4,5-trimethoxyphenoxy)benzamide;
N-cyclohexyl-N-cyclopentyl-4-(3,4-dimethoxyphenoxy)benzamide;

N-cyclohexyl-4-(3,4-dimethoxyphenoxy)-N-(1-methylethyl)benzamide;

N,N-dicyclopentyl-4-(3,4-dimethoxyphenoxy)benzamide;

N-cyclohexyl-4-[(3,4-dimethoxyphenyl)hydroxymethyl]-N-(1-methylethyl)benzamide;

N-cyclohexyl-N-cyclopentyl-4-[(3,4-dimethoxyphenyl)hydroxymethyl]-benzamide;

N,N-dicyclopentyl-4-[(3,4-dimethoxyphenyl)hydroxymethyl]benzamide;

N,N-dicyclopentyl-4-[(3,4-dimethoxyphenyl)methyl]-benzamide;

N-cyclohexyl-4-(3,5-dimethoxyphenoxy)-N-(1-methylethyl)benzamide;

N-cyclohexyl-N-cyclopentyl-3-methyl-4-(3,4,5-trimethoxyphenoxy)-benzamide;

N-cyclohexyl-4-[hydroxy(3,4,5-trimethoxyphenyl)methyl]-N-(1-methylethyl)benzamide;

N-cyclohexyl-N-(1-methylethyl)-4-[(3,4,5-trimethoxyphenyl)methyl]-benzamide;

N-cyclohexyl-N-(1-methylethyl)-4-(3,4,5-trimethoxybenzoyl)-benzamide;

N-cyclohexyl-N-cyclopentyl-4-[(2,4,5-trimethoxyphenyl)methyl]-benzamide;

N-cyclohexyl-4-(3,4-methylenedioxyphenoxy)-N-(1-methylethyl)benzamide;

N-cyclohexyl-3-methoxy-N-(1-methylethyl)-4-(3,4,5-trimethoxyphenoxy)benzamide;

N-cyclohexyl-4-[(2,4-dimethoxyphenoxy)methyl]-3-methoxy-N-(1-methylethyl)benzamide;

N-cyclohexyl-3-methoxy-4-[(3-methoxyphenoxy)methyl]-N-methylethyl)benzamide;

N-cyclohexyl-4-[(3-methoxyphenoxy)methyl]-N-methylbenzamide; and

N-cyclohexyl-N-methyl-4-[(3,4,5-trimethoxyphenoxy)methyl]benzamide; and a pharmaceutically acceptable carrier.

* * * * *

UNITED STATES PATENT AND TRADEMARK OFFICE
CERTIFICATE OF CORRECTION

PATENT NO. : 5,223,539

DATED : June 29, 1993

INVENTOR(S) : Nosal et al

It is certified that error appears in the above-indentified patent and that said Letters Patent is hereby corrected as shown below:

On the title page: Item [22] Filed: "Nov. 21, 1991" should read -- Nov. 22, 1991--.

Signed and Sealed this

Twelfth Day of April, 1994

*Attest:*

*Attesting Officer*

BRUCE LEHMAN

*Commissioner of Patents and Trademarks*